United States Patent
Graham et al.

(10) Patent No.: US 6,321,163 B1
(45) Date of Patent: Nov. 20, 2001

(54) METHOD AND APPARATUS FOR ANALYZING NUCLEIC ACID SEQUENCES

(75) Inventors: James R. Graham, Somerville; Kamalakar Gulukota, Westborough, both of MA (US)

(73) Assignee: Genetics Institute, Inc., Cambridge, MA (US)

( * ) Notice: Subject to any disclaimer, the term of this patent is extended or adjusted under 35 U.S.C. 154(b) by 0 days.

(21) Appl. No.: 09/389,092

(22) Filed: Sep. 2, 1999

(51) Int. Cl.[7] .................................................. G01N 33/48
(52) U.S. Cl. ............................. 702/19; 702/20; 702/21; 435/6; 435/91.2; 536/23
(58) Field of Search .................................. 435/6; 702/19, 702/20, 21

(56) References Cited

U.S. PATENT DOCUMENTS 6,047,109 * 4/2000 Whittaker ................................ 395/13

OTHER PUBLICATIONS

Tiwari et al., Prediction of probable genes by Fourier analysis of genomic sequences: CABIOS vol. 13, pp. 263–270, 1997.*

Pennisi, E (1999), "Human Genome: Academic Sequencers Challenge Celera in a Sprint to the Finish," Science, 283, pp. 1822–1823.

Fickett, J.W. (1982), "Recognition of Protein Coding Regions in DNA Sequences," Nucleic Acids Research, vol. 10, pp. 5303–5318.

Gribskov, M., et al. (1984), "The Codon Preference Plot: Graphic Analysis of Protein Coding Sequences and Prediction of Gene Expression," Nucleic Acids Research, vol. 12, pp. 539–549.

Claverie, J.M., et al. (1990), "K–tuple Frequency Analysis: From Intron–Exon Discrimination to T–cell Epitope Mapping," Methods in Enzymology, vol. 183, pp. 237–252.

Uberbacher, E.C. and Mural, R.J. (1991), "Locating Protein–Coding Regions in Human DNA Sequences by Multiple Sensor Neural Network Approach," Proceedings of the National Academy of Sciences, U.S.A., vol. 88, pp. 11261–11265.

Yan, M., et al. (1998), "A New Fourier Transform Approach for Protein Coding Measure Based on the Format of the Z Curve," Bioinformatics, vol. 14, pp. 685–690.

Tiwari, S., et al. (1997), "Prediction of Probable Genes by Fourier Analysis of Genomic Sequences," CABIOS, vol. 13, pp. 263–270.

Zhang, M.Q. (1997), "Identification of Protein Coding Regions in the Human Genome by Quadratic Discriminant Analysis," Proceedings of the National Academy of Sciences, U.S.A., vol. 94, pp. 565–568.

Burge, C. and Karlin, S. (1997), "Prediction of Complete Gene Structures in Human Genomic DNA," Journal of Molecular Biology, vol. 268, pp. 78–94.

Neubauer, G., et al. (1998), "Mass Spectrometry and EST–database Searching Allows Characterization of Multi–protein Sliceosome Complex," Nature Genetics, vol. 20, pp. 46–50.

Gelfand, M.S., et al. (1996), "Gene Recognition Via Spliced Sequence Alignment," Proceedings of the National Academy of Sciences, U.S.A., vol. 93, pp. 9061–9066.

Chan et al., "On computing the discrete cosine and sine transf orms from the discrete Fourier transform," International Symposium on Computer Architecture and digital Signal Processing, CA–DSP 1989, Hong Kong, 1:363–366 (1989).

Benson, "Fourier methods for biosequence analy sis," Nucleic Acids Research, 18:21, pp. 6305–6310 (1990).

Yan, et al., "A new Fourier transf orm approach for protein coding m easure based on the format of the Z curve," Bioinformatics, Oxford University Press, 14:8, pp. 685–690 (1998).

Benson, "Digital signal processing m ethods for biosequence com parison," Nucleic Acids Research, 18:10, pp., 3001–3006 (1990).

Fickett, "Finding genes by computer: the state of the art, "Trends in Genetics, NL, Elsev ier Science Publishers B. V. Am sterdam, 12:8, pp. 316–320 (Aug. 1, 1996).

* cited by examiner

*Primary Examiner*—John S. Brusca
*Assistant Examiner*—Jeffrey S. Lundgren
(74) *Attorney, Agent, or Firm*—Finnegan, Henderson, Farabow, Garrett & Dunner, L.L.P.

(57) ABSTRACT

A method and apparatus are disclosed for identifying protein-coding regions in a nucleic acid sequence. In order to predict the coding regions within a sequence, a single metric is used without reference or comparison to a predetermined noise level or signal-to-noise ratio. This single metric, periodicity at $1/3$, is analyzed using a discrete cosine transformation (DiCTion) function. For each open reading frame or sequence region, a score is generated using the discrete cosine transformation function. Regions within a sequence that have a score above a predetermined threshold are identified as protein-coding regions. The aspects of the invention may also be applied to gather other information from sequences, such as the location of the borders of a putative coding region, within a genomic sequence.

44 Claims, 14 Drawing Sheets

METHOD AND APPARATUS FOR ANALYZING NUCLEIC ACID SEQUENCES

BACKGROUND OF THE INVENTION

I. Field of the Invention

The present invention generally relates to the field of genomic research and to the use of computational tools for analyzing nucleic acid sequences. More particularly, the present invention relates to computer- and software-based tools for discriminating protein-coding regions from non-coding regions in a sequence, and for analyzing other properties of a nucleic acid sequence.

II. Background and Material Information

Vast amounts of sequence data have been collected in the scientific community as a result of various sequencing efforts. The complete genome sequence is already available for many prokaryotes, for yeast, and for the nematode Caenorhabditis elegans. Further, efforts to sequence the entire human genome continue to place large amounts of sequence data into public databases. In addition, other efforts to sequence the genomes of other organisms, like the mouse, will generate additional sequence data for the scientific community. Recently established commercial ventures also promise to accelerate the pace of genomic sequencing even further (see, for example, PENNISI, E. (1999), "Human Genome: Academic Sequencers Challenge Celera in a Sprint to the Finish," *Science*, 283, pp.1822–1823).

The deluge of sequence data has created a need for automated processes for deriving useful information from sequences. In particular, there is a critical need for computational tools that do not require human intervention and that provide a high processing throughput. For example, in the area of genomic research, there is a strong need for reliable computational tools that provide an automated process for identifying protein-coding genes in deoxyribonucleic acid (DNA) sequences. The ability to accurately identify protein-coding regions from non-coding regions in a sequence is a critical aspect of the overall process for developing therapeutic compounds and drugs for treating human diseases.

Several approaches have been proposed for gene detection. One approach for determining the coding potential of DNA sequences has been to look for patterns that distinguish coding sequences from non-coding sequences. Such approaches look for the predominant occurrence of a given base at specific codon positions and/or the presence of other characteristics in order to identify protein-coding regions within a DNA sequence (see, for example, FICKETT, J. W. (1982), "Recognition of Protein Coding Regions in DNA Sequences," *Nucleic Acids Research*, Vol.10, pp. 5303–5318). In the approach proposed by FICKETT, preference numbers are computed for all four bases (i.e., Adenine (A), Cytosine (C), Guanine (G), and Thymine (T)) at each of the three codon positions to generate a total of twelve numbers. By establishing the characteristic values of these twelve numbers among coding and non-coding sequences, the FICKETT approach attempts to identify protein-coding regions within a DNA sequence.

Codon preference approaches (see, for example, GRIBSKOV, M., et al., (1984), "The Codon Preference Plot: Graphic Analysis of Protein Coding Sequences and Prediction of Gene Expression," *Nucleic Acids Research*, Vol. 12, pp. 539–549) typically exploit the fact that species differ in their preference for using certain codons for certain amino acids. Codon usage tables have been prepared for a variety of species. Under this approach, the adherence to the usage characteristics of the species in question is considered an indication that the given sequence is a coding region. However, codon preferences relate to the availability of specific transfer ribonucleic acids (tRNAs) in the cell. Therefore, strict adherence to a codon frequency table is much more likely for highly expressed genes, than for genes of lower expression levels.

Other methods have been proposed for identifying protein-coding regions based on the preferential occurrence of specific "words" in a sequence. For example, one approach has relied upon the preferential occurrence of specific words having two or six nucleotides within coding regions as a means of predicting the coding potential of DNA sequences (see, for example, CLAVERIE, J. M., et al. (1990), "K-tuple Frequency Analysis: From Intron-Exon Discrimination to T-cell Epitope Mapping," *Methods in Enzymology*, Vol. 183, pp. 237–252).

Neural networks and neural net trained systems have also been proposed for identifying protein-coding regions in sequences. For example, GRAIL uses various sensor algorithms based on past approaches and a modified version of the nucleotide word occurrence approach to predict coding regions (see, for example, UBERBACHER, E. C. and MURAL, R. J. (1991), "Locating Protein-Coding Regions in Human DNA Sequences by Multiple Sensor Neural Network Approach", *Proceedings of the National Academy of Sciences*, U.S.A., Vol. 88, pp. 11261–11265). In GRAIL, the output from each sensor algorithm is provided as input to a neural network that is trained to predict coding from non-coding sequences based on the output from the sensor algorithms. The neural network of GRAIL purportedly provides a higher prediction value than any one of the sensor techniques individually.

While such techniques have been proposed, all of the past approaches share at least two major drawbacks. First, past approaches use a sliding window that is generally insufficient in length to provide a reliable computational tool. For example, past approaches typically use a sliding window that is between 50 to 200 nucleotides. A sliding window of this length is insufficient to make statistically significant conclusions. Further, the use of longer windows in past approaches is not feasible since it reduces the resolution of the technique. Second, all of the above-noted approaches are dependent on statistical data collected from a sequence database. Since any such database, of necessity, contains only known genes, this may imply a systematic bias toward the genes of relatively high expression.

In an attempt to address the first drawback, a Fourier transform method has been developed that amplifies any periodicities that are found in order to effectively lengthen the window size (see, for example, YAN, M., et al. (1998), "A New Fourier Transform Approach for Protein Coding Measure Based on the Format of the Z Curve, *Bioinformatics*, Vol. 14, pp. 685–690). Further, in an attempt to address the second drawback, a technique referred to as GeneScan moves away from dependence on any preexisting databases by noticing a peak signal at a frequency of ⅓ in the Fourier transform of most coding regions (see, for example, TIWARI, S., et al., (1997), "Prediction of Probable Genes by Fourier Analysis of Genomic Sequences", CABIOS, Vol.13, pp. 263–270). In GeneScan, the DNA sequence is subjected to a Fourier transform analysis and the presence of a signal that is significantly above a noise level is examined. Any window that shows such a signal is predicted by GeneScan to be a protein-coding region.

While such techniques have been proposed, past approaches still suffer significant drawbacks. For example, the window size employed in GeneScan (i.e., 99 nucleotides) is likely to be inadequate to observe the peak signal for all sequences. Further, the requirement in GeneScan that the signal be significantly above noise may not be required and may impose an unnecessary constraint on the analysis process. Further, and perhaps more importantly, none of the proposed methods eliminate both of the major drawbacks of past approaches and provide a process that has a high degree of reliability for analyzing various types of sequences.

In view of the foregoing, there is presently a need for a process or system for analyzing sequence data that is not dependant on any preexisting databases and that eliminates the use of a sliding window. There is also a need for computational tools that use all available information, and that provide more robust pattern detection capabilities. In addition, there is a need for automated processes or systems for identifying protein-coding regions of a nucleic acid sequence while providing a high level of reliability for various types of species and patterns. Such features would enable researchers and other members of the scientific community to analyze sequence data in a more efficient and reliable manner, and facilitate the process for developing new drugs and remedies for diseases.

SUMMARY OF THE INVENTION

In what follows, a "genomic DNA sequence" refers to a DNA sequence from genetic DNA, before it is transcribed. Further, a "complementary DNA (cDNA) sequence" refers to a sequence of a DNA molecule that is complementary to a mature messenger RNA (mRNA), i.e., it is presumed to contain no introns. A "putative coding region" is defined as a region within a cDNA or genomic DNA sequence which could be a coding region. Specifically, the region is identified through sequence based methods which may have many false positives but very few false negatives. For example, in a cDNA sequence, a putative coding region may be defined as any stretch of sequence that begins in a start codon (or initiation codon) and ends in a stop codon (or termination codon). Such a stretch is called an open reading frame (ORF). For a sequence which uses the universal genetic code, the initiation codon is typically ATG (AUG for mRNA), but it may also be GTG (GUG for mRNA). In the universal genetic code, the termination codon is one of TAA (UAA in mRNA), TAG (UAG in mRNA) or TGA (UGA in mRNA). When another genetic code is in play (e.g., when mitochondrial sequences are analyzed), the appropriate code must be utilized for initiation and termination codons. In a genomic DNA sequence, putative coding regions are exons. Therefore, they do not necessarily begin in initiation codons nor do they necessarily end in termination codons. However, they cannot cross in-frame termination codons. Therefore, for a genomic DNA sequence, a putative coding region is a stretch of sequence from just after a termination codon to the next in-frame termination codon. This is referred to as a stop-stop stretch (SSS).

In accordance with the principles of the present invention, embodied and broadly described herein, a method and apparatus are provided for analyzing nucleic acid sequences based on a modified discrete cosine transformation technique (referred to as "DiCTion"). The features and aspects of the present invention are not dependent on any preexisting database. In addition, the invention does away with use of any type of sliding window and instead uses all the sequence within a putative coding region or open reading frame (ORF). As a result, the present invention uses the maximum amount of sequence and gives rise to a more robust technique for gene detection. Further, as illustrated by the examples disclosed herein, the features of the present invention provide improved sensitivity and improved specificity for databases containing coding and non-coding sequences.

The present invention achieves this clean separation through the use of a periodic function, a modified discrete cosine transformation (DiCTion) which is disclosed herein. However, other periodic functions may be used in the place of DiCTion to obtain comparable or slightly inferior results. Examples of other functions include Fourier transformation, cosine transformation, and other functions that can be substituted by those of ordinary skill in the art in view of the present disclosure.

One preferred embodiment of the invention involves the use of a modified discrete cosine transformation function for identifying protein-coding regions for any genomic DNA sequence, cDNA sequence or RNA sequence. The features of the present invention also provide a unique process and system for analyzing the borders of protein-coding regions within a sequence and for analyzing the sequences of genes.

In accordance with an embodiment of the present invention, a method and apparatus are provided for predicting protein-coding regions in a nucleic acid sequence. In order to predict the coding regions within a sequence, a single metric (e.g., periodicity at a frequency of $\frac{1}{3}$) is used without reference or comparison to a predetermined noise level or signal-to-noise ratio. This single metric can be analyzed using the discrete cosine transformation function of the present invention for a putative region (e.g., an open reading frame). For each region, a score is generated using the discrete cosine transformation function (referred to as the "DiCTion score"). Regions within a sequence that have a score above a predetermined threshold (e.g., 1.0 or 1.5) may be flagged or identified as corresponding to a protein-coding region. In a cDNA sequence only one real ORF is expected even though the ORF may be split in two by a frame shift caused by a sequence error, as discussed in greater detail below. As such, if a cDNA sequence is determined to have more than one region with a score above the predetermined threshold, then other criteria may be used to choose among them. The simplest of these is length. Therefore, the longest region with a score above the threshold may be identified as corresponding to a protein-coding region. Other criteria include expressed sequence tag (EST) matching and protein homology.

According to another aspect of the present invention, a method and apparatus are provided for predicting borders of protein-coding regions within a sequence. The border detection techniques may be utilized for determining where a coding region begins and ends. As part of this technique, the discrete cosine transformation function of the present invention may be applied to determine the score of the sequence between two arbitrary borders or anchors (k1 and k2) that are independently moved until a maximum score is reached. As further disclosed herein, this aspect of the invention may be applied to identify the entire coding sequence.

In accordance with still another aspect of the invention, a method is provided for analyzing a nucleic acid sequence. The method comprises: providing a nucleic acid sequence data; identifying each open reading frame (ORF) of the sequence based on the nucleic acid sequence data; calculating a score for each identified ORF of the sequence; comparing the calculated score of each ORF to a predetermined threshold; and identifying a protein-coding region in the nucleic acid sequence based on the comparison of the score of each ORF to the predetermined threshold.

In the method of the invention for analyzing a nucleic acid sequence, the protein-coding region may be identified by identifying each ORF having a score greater than or equal to a predetermined threshold (e.g., 1.0 or 1.5) as corresponding to a coding region. Further, the score of each ORF may be determined by examining and scoring the periodicity of each base in the ORF at a frequency of ⅓ based on a periodicity function (e.g., the DiCTion function). An index of each ORF may also be determined based on the index assigned to the first base of each ORF that provides a maximum score. In such a case, the score for each ORF may be set to the maximum score at the index.

The present invention also relates to a computer program product comprising computer-readable media having computer-readable code which, when run on a computer, causes the computer to analyze a nucleic acid sequence based on sequence data. The computer program product may include, for example, the following computer-readable program code for effecting actions in the computer: program code for identifying predetermined regions (e.g., an ORF, SSS region, or region between splice sites) of the nucleic acid sequence based on the sequence data; program code for calculating a score for each identified region of the nucleic acid sequence; program code for comparing the calculated score of each region to a predetermined threshold and for determining whether the score of each region is greater than or equal to the predetermined threshold; and program code for identifying at least one coding region in the nucleic acid sequence based on the score of each region that is determined to be greater than or equal to the predetermined threshold.

In the computer program product, the program code for identifying predetermined regions may comprise program code for locating each region of the nucleic acid sequence that is between pairs of related termination codons or between an initiation codon and an in-frame termination codon. Alternatively, each predetermined region in the sequence can be identified through program code for locating each region of the nucleic acid sequence that is between intron-donor and intron-acceptor sites (hereinafter referred to as "splice sites"). Further, the computer program product may comprise program code for examining the periodicity of each base in the identified region at a frequency of ⅓ and scoring the periodicity of each base in the identified region based on a discrete cosine transformation function or another suitable function.

According to another aspect of the invention, a method is provided for detecting borders of a coding region in a nucleic acid sequence. The method comprises: identifying a coding region in the nucleic acid sequence from a set of sequence data; setting two anchor locations in the identified coding region of the nucleic acid sequence; calculating a score for the portion of the nucleic acid sequence between the two anchor locations; moving one of the two anchor locations along the nucleic acid sequence by one codon; repeating the steps of calculating and moving until a maximum score is reached for the portion of the nucleic acid sequence between the two anchor locations; and identifying at least one border of the coding region based on the position of one of the two anchor locations in the nucleic acid sequence where a maximum score is reached.

In the method for detecting borders, the step of calculating a score may comprise scoring the periodicity of each base in the identified coding region at a frequency of ⅓ in accordance with a periodicity function (e.g., the DiCTion function). The identified region may correspond to an open reading frame (ORF) or regions of the sequence that are between termination codons or splice sites. Further, the step of setting anchor locations in the method of the present invention may comprise setting the two anchor locations at a predetermined minimum distance from one another along the nucleic acid sequence.

According to still another aspect of the invention, a method is provided for locating exons within a sequence of a gene. The method comprises: identifying at least one region in the sequence of the gene; calculating a score of each region in the sequence; and determining the location of each exon in the sequence based on the score of each region of the sequence. In the disclosed method, the step of identifying may comprise identifying each stop-stop stretch (SSS) region in the sequence of the gene and the step of calculating may comprise scoring the periodicity of each base in each SSS region at a frequency of ⅓ in accordance with a periodicity function. Further, the score of each SSS region in the sequence may be compared to a predetermined threshold and an SSS region may be identified as containing an exon if the score of the SSS region is greater than or equal to the predetermined threshold.

Alternatively, in the method for locating exons the step of identifying may comprise identifying at least one jumping window region in the sequence of the gene and the step of calculating may comprise scoring the periodicity of each base in each jumping window region at a frequency of ⅓ in accordance with a periodicity function. In such a case, the score of each jumping window region in the sequence may be compared to a predetermined threshold and a jumping window region may be flagged if the score of the jumping window region is greater than or equal to the predetermined threshold. Further, the borders of each flagged jumping window region may be expanded until a maximum score for the region is reached and the location of an exon in the sequence may be identified based on the longest, expanded jumping window.

In accordance with another aspect of the invention, a method is provided for determining whether a predetermined region of a nucleic acid sequence is full length. The method comprises: identifying a portion of the nucleic acid sequence that is upstream of the predetermined region of the sequence; calculating a score for the upstream portion of the nucleic acid sequence; and determining whether the predetermined region is full length based on the calculated score of the upstream portion of the nucleic acid sequence. In the disclosed method, the step of determining may comprise comparing the score of the upstream portion of the sequence to a predetermined threshold, and determining that the predetermined region is full length if the score of the upstream portion of the sequence is less than the predetermined threshold. Further, the step of determining may further comprise determining that the predetermined region is not full length if the score of the upstream portion of the sequence is greater than or equal to the predetermined threshold.

In accordance with yet another aspect of the invention, a method is disclosed for determining whether a predetermined region of a nucleic acid sequence is full length. The method preferably comprises: identifying a portion of the nucleic acid sequence that is upstream or downstream of the predetermined region of the sequence; combining the upstream or downstream portion of the sequence to the predetermined region of the sequence and calculating a score for the combined region; and determining whether the predetermined region is full length based on the calculated score of the combined region. The method may also include calculating a score of the predetermined region of the sequence, and the step of determining may comprise comparing the score of the combined region with the calculated score of the predetermined region and determining that the predetermined region is full length if the score of the predetermined region is greater than the score of the combined region. In addition, the step of determining may further comprise determining that the predetermined region is not full length if the score of the predetermined region is less than the score of the combined region.

It is to be understood that both the foregoing general description and the following detailed description are exemplary and explanatory only and are not restrictive of the invention, as claimed. Further features and/or variations may be provided in addition to those set forth herein. For example, the present invention may be directed to various combinations and subcombinations of the disclosed features and/or combinations and subcombinations of several further features disclosed below in the detailed description.

BRIEF DESCRIPTION OF THE DRAWINGS

The accompanying drawings, which are incorporated in and constitute a part of this specification, illustrate various embodiments and/or features of the invention and together with the description, serve to explain the principles of the invention. In the drawings.

DETAILED DESCRIPTION

Systems and methods consistent with the principles of the present invention overcome the shortcomings of prior research approaches by providing techniques for analyzing nucleic acid sequences and identifying, with a high degree of reliability, protein-coding regions, such as exons, and non-coding regions, such as introns, within a sequence. The aspects of the invention can also be utilized to determine other characteristics of a sequence, such as the borders of coding and non-coding regions within a particular sequence. As further disclosed below, such systems and methods are well-suited for identifying, for example, protein-coding regions within a cDNA sequence, a genomic DNA sequence or any other type of RNA or DNA sequence. The features of the present invention may also be applied in various applications for identifying the borders of coding and non-coding regions within a sequence, such as the 5' borders and the 3' borders for genomic DNA sequences containing introns and exons.

The above-noted features and other aspects and principles of the present invention may be implemented in various system or network environments to provide automated computational tools to facilitate sequence data research and analysis. Such environments and applications may be specially constructed for performing the various processes and operations of the invention or they may include a general purpose computer or computing platform selectively activated or reconfigured by program code to provide the necessary functionality. The processes disclosed herein are not inherently related to any particular computer or other apparatus, and may be implemented by any suitable combination of hardware, software, and/or firmware. For example, various general purpose machines may be used with programs written in accordance with the teachings of the invention, or it may be more convenient to construct a specialized apparatus or system to perform the required methods and techniques. The present invention also relates to computer readable media that include program instructions or program code for performing various computer-implemented operations based on the methods and processes of the invention. The media and program instructions may be those specially designed and constructed for the purposes of the invention, or they may be of the kind well known and available to those having skill in the computer software arts. Examples of program instructions includes both machine code, such as produced by compiler, and files containing a high level code that can be executed by the computer using an interpreter.

Figure 1:
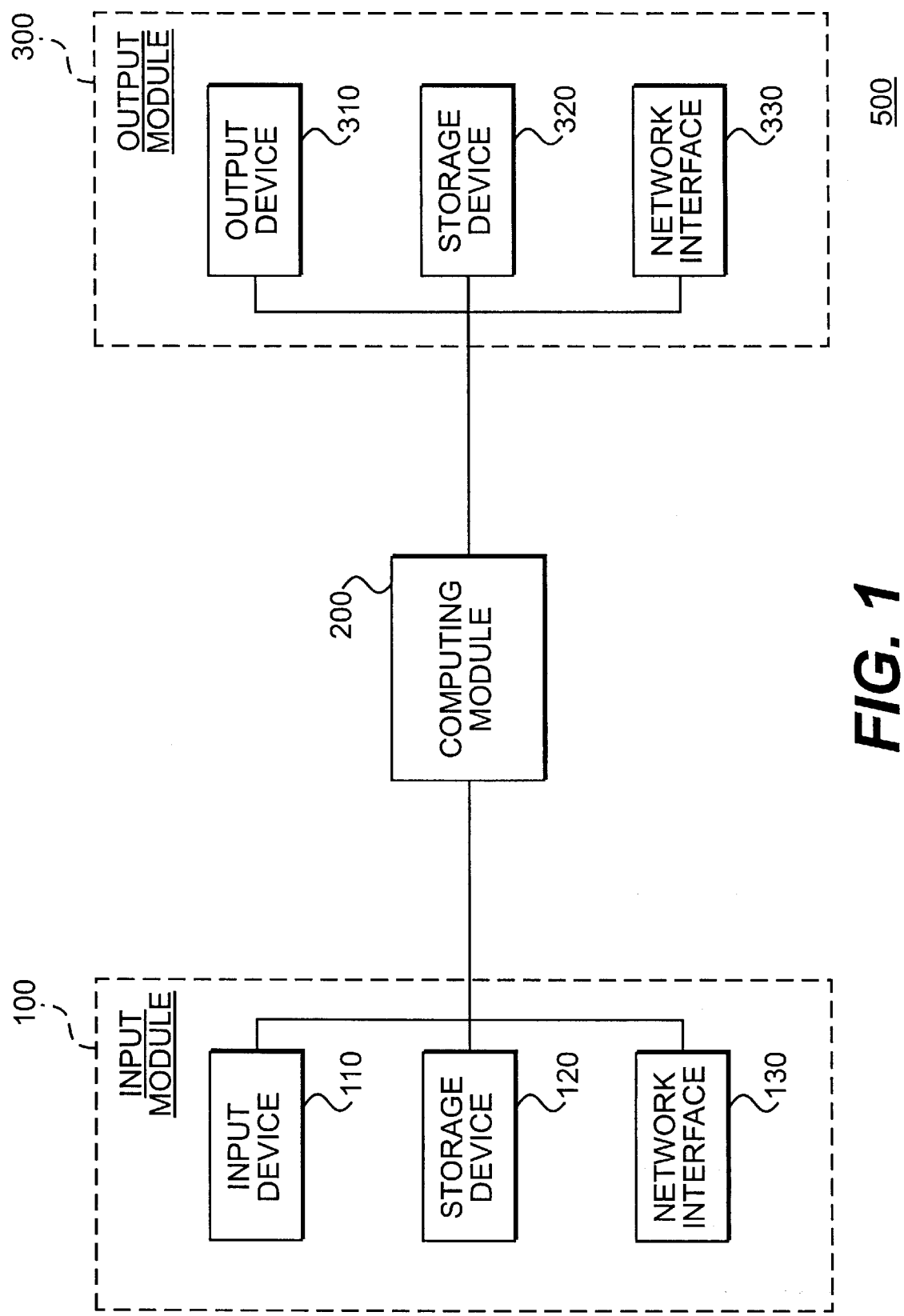
FIG. 1 illustrates, in general block diagram form, a system environment in which the various features and aspects of the present invention may be implemented.

By way of a non-limiting example, FIG. 1 illustrates a system environment 500 in which the features and principles of the present invention may be implemented. As illustrated in the block diagram of FIG. 1, system environment 500 includes an input module 100, a computing module 200, and an output module 300. Computer module 200 is adapted to provide the necessary functionality and computing capabilities to analyze sequence data provided from input module 100. The result(s) of analyzing the sequence data are provided as output from computing module 200 to output module 300. The analysis performed by computing module 200 may include identifying protein-coding regions in a sequence, the detection of borders in a sequence, and the determination of various other characteristics and information from sequence data, as further disclosed herein with reference to the accompanying drawings.

In the embodiment of FIG. 1, computing module 200 may comprise a computer-based platform or processing system for performing various functions and operations of the invention. Computing module 200 may be implemented, for example, by a general purpose computer selectively activated or reconfigured by a computer program stored in the computer, or may be a specially constructed computing platform for carrying-out the features and operations of the present invention. Computing module 200 may also implemented or provided with a wide variety of components or subsystems including, for example, one or more of the following: one or more central processing units, a co-processor, memory, registers, and other data processing devices and subsystems. Computing module 200 communicates or transfers data to and from input module 100 and output module 200 through the use of direct connections or communication links, as illustrated in FIG. 1, or through the use of a network architecture (not shown). Such a network architecture may comprise a local area network (LAN), a wide area network (WAN), a dedicated intranet, and/or the Internet. Further, any suitable combination of wired and/or wireless components and systems may be incorporated into such a network architecture. By using dedicated communication links or a shared network architecture, computing module 200 may be located in the same location or at a geographically distant location from input module 100 and/or output module 300.

Input module 100 of system environment 500 may be implemented with a wide variety of devices to receive and/or provide the sequence data as input to computing module 200. As illustrated in FIG. 1, input module 100 includes an input device 110, a storage device 120, and/or a network interface 130. Input device 110 may comprise a keyboard, a mouse, a disk drive, a sequencing machine (e.g., an automatic sequencing device manufactured by ABI or another type of sequencing device) or any other suitable input device for providing sequence data to computing module 200. Storage device 120 may be implemented with various forms of memory or storage devices, such as read-only memory (ROM) devices and random access memory (RAM) devices. Storage device 120 may store large volumes of sequence data to provide as input to computing module 200. Input module 100 may also include network interface 130, as illustrated in FIG. 1, to receive sequence data over a network (such as a LAN, WAN, intranet or the Internet) and to provide the same as input to computing module 200. For example, network interface 130 may be connected to a public database over a network for the purpose of receiving and transferring sequence data to computing module 200.

Output module 300 includes an output device 310, a storage device 320, a network interface 330, and/or other devices for receiving the results provided as output from computing module 200. For example, output device 310 may be implemented as a display device, a printer or any other type of device capable of communicating the results from computing module 200 to, for example, a researcher or user. Storage device 320 may be implemented with a storage device, database or other suitable memory device capable of storing the results from computing module 200. In accordance with an aspect of the invention, a network interface, such as network interface 330, may be provided in output module 300 in order to facilitate the communication of the results from computer module 200 over a network (such as a LAN, WAN, intranet or the Internet) for viewing or analysis by an end user.

According to an aspect of the invention, a technique is provided for detecting protein-coding regions in a nucleic acid sequence. This technique relies on several features, including the application of a discrete cosine transformation (DiCTion) function. This aspect of the invention does away with use of any type of sliding window and is not dependent on preexisting databases. Instead, the present invention permits the use of the maximum amount of the sequence, and provides more robust pattern detection capabilities for DNA sequences, such as genomic DNA and cDNA sequences.

In order to identify protein-coding regions within a nucleic acid sequence, implementations consistent with the present invention utilizes a single metric to distinguish coding from non-coding regions. This single metric is the periodicity of each base (Adenine (A), Cytosine (C), Guanine (G), and Thymine (T)) in the sequence at a frequency of ⅓. The periodicity of bases in RNA sequences (A, C, G and Uracil (U)) can similarly be used. In either case, this periodicity in a nucleic acid sequence, as measured by the discrete cosine transformation function of the invention, is highly correlated with the coding potential of the sequence. Using the discrete cosine transformation function of the invention, the periodicity in a sequence at a frequency of ⅓ can be examined without resorting to computing a signal to noise ratio to determine the significance of the signal. Further, by using the entire sequence of a putative region (e.g., an open reading frame (ORF), or a region between two termination codons or splice sites) errors caused by relying upon a sliding window are minimized.

In general, distinguishing between coding and non-coding regions may be accomplished in accordance with the principles of the invention through the following main steps: (i) identifying putative coding regions in the sequence; (ii) examining the periodicity and calculating a score for each identified region; and (iii) identifying protein-coding regions in the sequence based on the identified regions that have a score that is greater than or equal to a predetermined threshold.

In the first step, each putative region in a given sequence is identified. For a cDNA sequence, this step may entail identifying each open reading frame (ORF) in the sequence. An ORF is a stretch of potential codons that may encode an amino acid sequence. An ORF may be identified by locating an initiation or start codon, and a termination or stop codon that is in-frame. For genomic sequences, this step may entail locating regions of the sequence that are between pairs of termination codons or that are between splice sites, as further described below.

After identifying every putative region in the sequence, a score is calculated for each identified region using, for example, the discrete cosine transformation (DiCTion) function. During this second step, the periodicity of each base in the ORF or identified region is examined at a frequency of ⅓. A score for the ORF or identified region may be computed by determining an index of each ORF or region, as will be discussed in greater detail below.

In the third and final step, each ORF or identified region with a score greater than a predetermined threshold (e.g., 1.0 or 1.5) is identified as being a coding region. If more than one ORF or region has a score above the threshold, then the longest ORF or region with a score above the threshold may be identified as coding. If none of the regions in the sequence has a score above the threshold, then the sequence is identified as being a non-coding sequence.

In accordance with the present invention, the discrete cosine transformation (DiCTion) score at a frequency F of a nucleotide sequence region of N nucleotides is determined in accordance with the following equation:

$$D(F) = \frac{1}{N} \sum_\alpha \left| \sum_{j=1}^{N} U_\alpha(j) \cos(2\pi F j) \right|^2$$

where D(F) is the DiCTion score, N is the number of nucleotides in the sequence region, α varies over four bases (A, C, G, T or U), j is the position in the sequence region and $U_\alpha(j)$ is similar to a delta function, as defined below. In order to inspect the periodicity of each of the bases at a frequency of ⅓, the frequency F is set to ⅓. However, in principle, it is possible to calculate the full spectrum.

When inspecting a nucleic acid sequence, four binary streams are generated using the delta function ($U_\alpha(j)$) representing each of the four nucleotides or bases. The delta-like function ($U_\alpha(j)$) is defined as 1 if the base at the $j^{th}$ position in the sequence is α and defined as 0 otherwise. Consider, for example, the following DNA sequence:
'GAATTC'
For the above DNA sequence, the four binary streams generated with the delta function ($U_\alpha(j)$) are as follows:

| α | 'G A A T T C' |
|---|---|
| A | 0 1 1 0 0 0 |
| C | 0 0 0 0 0 1 |
| G | 1 0 0 0 0 0 |
| T | 0 0 0 1 1 0 |

Each of these sequences is iterated through and the value (1 or 0) is multiplied by the cosine term (i.e., $\cos(2\pi Fj)$). Each of the streams are then squared, summed together and multiplied by a normalization factor which is 1/N, where N is the number of nucleotides in the sequence region.

Since the cosine function is periodic, a phase is implied in the DiCTion function of the present invention. Specifically, the DiCTion value of a sequence will depend on the index of the first nucleotide. That is, the same sequence will have different DiCTion values depending on whether the nucleotides are numbered from 0 to N−1, from 1 to N, or from 2 to N+1. At a frequency F of ⅓, numbering the nucleotides from 3 to N+2 will yield the same DiCTion value as 0 to N−1, 4 to N+3, the same as 1 to N and so on. Therefore, when the frequency F=⅓, three distinct values can be obtained for the DiCTion value. Since the difference between the three values is the index of the starting nucleotide, which is an arbitrary choice, these differences are immaterial. Therefore, according to an aspect of the present invention, all three values are calculated (assigning the index of 1, 2, and 3 to the first nucleotide) with the maximum value being considered. In such a case, the corresponding index of the first base may be defined as the DiCTion index and the maximum score may be defined as the DiCTion score. In other words, the index assigned to the starting nucleotide that yields the maximum score may be referred to as the index for that particular ORF or identified sequence region.

To provide a better understanding of the features and aspect of the present invention, reference will now be made to the exemplary embodiments of FIGS. 2 and 3.

Figure 2:
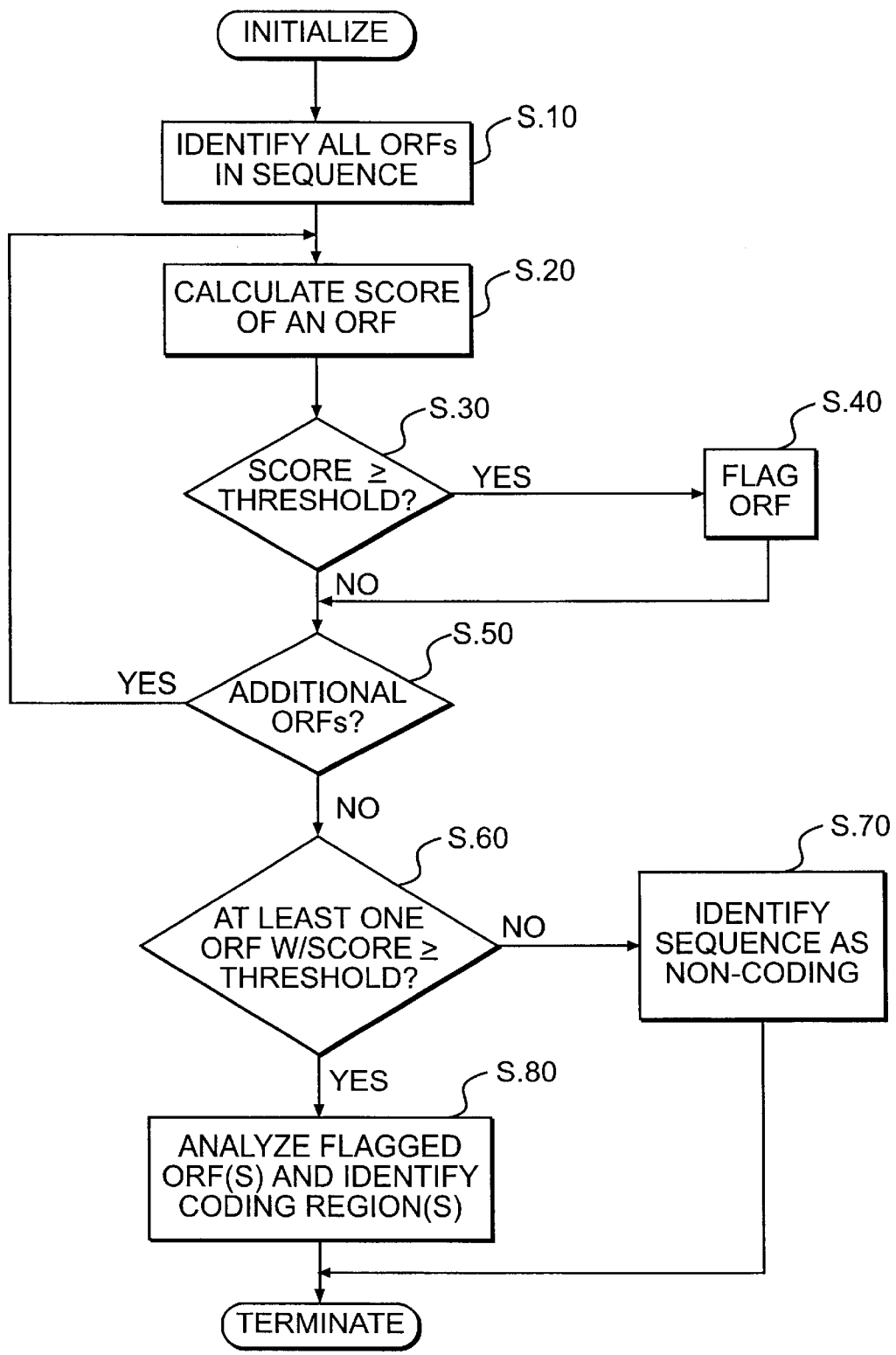
FIG. 2 is an exemplary flowchart of a process to analyze a nucleic acid sequence and identify coding regions within a sequence, in a manner consistent with the present invention.
Figure 3:
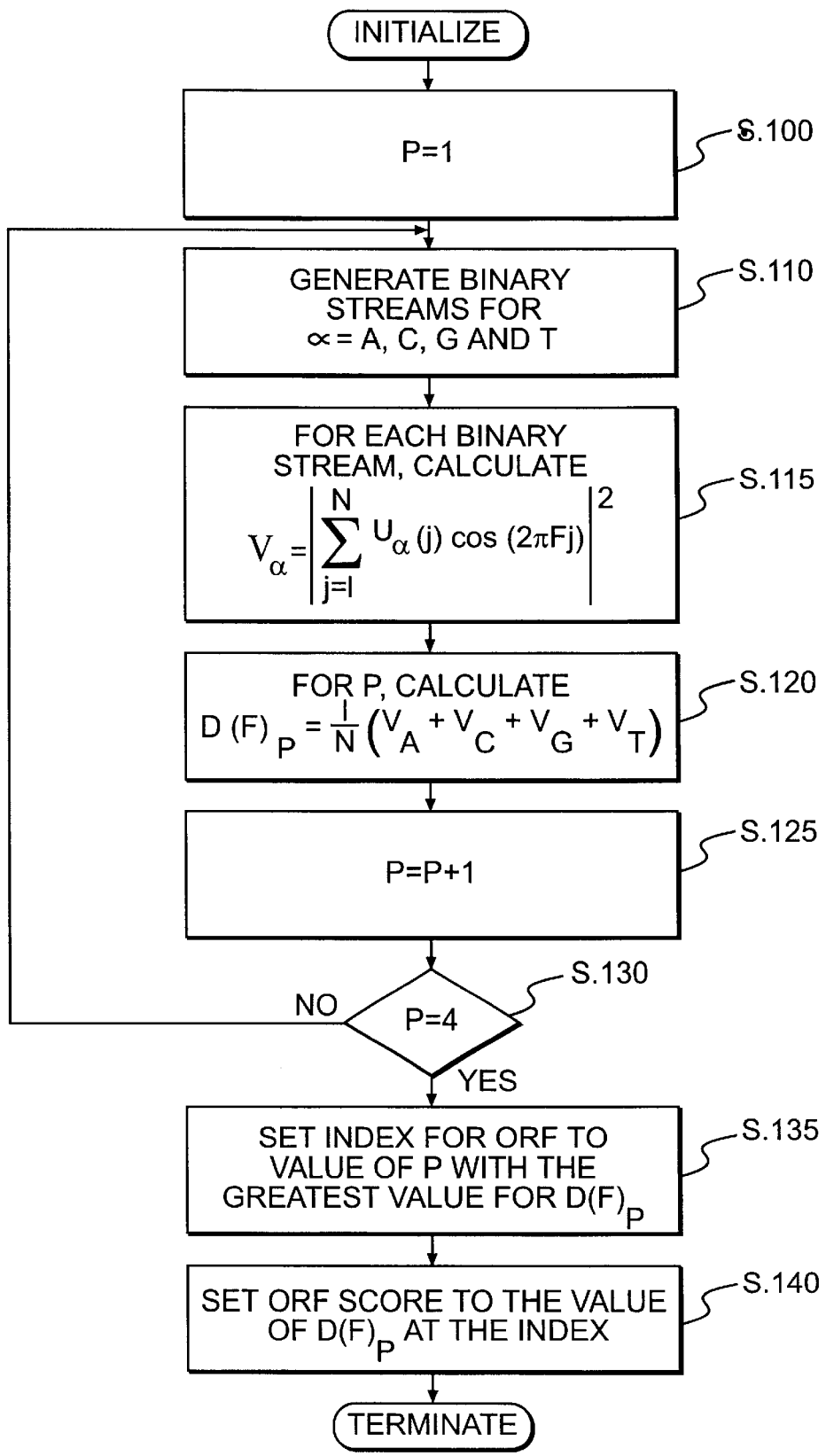
FIG. 3 is an exemplary flowchart of a process to calculate a score using the discrete cosine transformation function, in a manner consistent with the present invention.

FIGS. 2 and 3 are exemplary flowcharts of the various processes and operations to be performed in a network environment (such as network environment 500 of FIG. 1) for identifying protein-coding regions in a nucleic acid sequence. For purposes of illustration, FIGS. 2 and 3 illustrate the steps and operations for distinguishing between coding and non-coding regions in a sequence by analyzing all open reading frames (ORFs) in the sequence. As indicated above, an ORF is a stretch of potential codons that may encode an amino acid sequence and can be identified by locating an initiation codon and a downstream termination codon that is in-frame. The features of FIGS. 2 and 3 can be adapted and applied to any genomic DNA sequence by analyzing regions of the sequence between termination codons or splice sites instead of examining ORFs.

As illustrated in FIG. 2, the process is initiated by first identifying all ORFs in the sequence (step S.10). Each ORF may be identified by looking for every initiation codon and a downstream termination codon that is in-frame. After identifying each ORF, a score is calculated for every ORF (step S.20). The score of each ORF may be calculated based on the discrete cosine transformation (DiCTion) function. FIG. 3 is an exemplary flowchart of a process for calculating a score for each ORF using the DiCTion function.

The present invention is not limited to the DiCTion function disclosed herein. Other cosine based functions or Fourier transformation functions may be utilized to evaluate the periodicity of each of the bases in the sequence. However, in each case, the periodicity should be evaluated at a frequency of ⅓. This is because coding regions within a sequence produce a periodicity at a frequency of ⅓ that is, on average, at least an order of magnitude higher than that found in non-coding sequences.

After calculating the score of an ORF (step S.20), the value of the score is analyzed to determine whether it is greater than or equal to a predetermined threshold (step S.30). This threshold may be set based on the type of sequence that is being analyzed and/or the cosine-based function or transformation function that is used to calculate the score of the ORF. For example, for the DiCTion function, a threshold value of 1.0 or 1.5 is preferably utilized, as indicated below.

In order to determine the threshold value for a particular periodic function, an analysis can be performed based on one or more pre-existing databases. For example, the Bullet Train (BT) and Control DB databases may be utilized to analyze the accuracy provided by applying different threshold values. As indicated below, Bullet Train (BT) is a positive database that includes sequences which contain one coding ORF. Control DB, on the other hand, is a negative database that includes sequences that do not contain a coding ORF. A listing of the entries in the Control DB can be found over the Internet or from the European Bioinformatics Institute (EBI).

Bullet Train contains a list of human proteins from SwissProt (the version current as of July 1998) available from the Swiss Institute of Bioinformatics (SIB), in which no two proteins in the list show significant homology to each other. This non-redundancy in the Bullet Train database insures a wide representation of genes. The list was further pared down to exclude all proteins for which a full-length cDNA sequence was not available in genbank. A total of 405 cDNA sequences (i.e., 819,879 nucleotides) are present in Bullet Train.

The Control DB database consists of 5' and 3' untranslated regions (UTRs) of known genes. In total, there are 6,707 3' UTRs and 1,469 5' UTRs in the Control DB, as downloaded from the Internet in November 1998. The sequences in Control DB account for about 7.5 million bases of sequence.

As can be seen from Table 1, using a threshold value of 1.0 (i.e., sequences scoring greater than or equal to 1.0 being considered to be coding regions), a 96.5% accuracy in predicting coding ORFs can be achieved with DiCTion. However, this threshold value has an arguably unacceptable high false positive rate. On the other hand, using a threshold value of 1.5 (i.e., sequences scoring greater than or equal to 1.5 being considered to be coding regions), a accuracy level of 93% is provided for predicting protein-coding ORFs and the false positive rate drops to a more acceptable level.

The threshold chosen depends upon the needed sensitivity and specificity of the application under development. For most purposes, a threshold of 1.5 for DiCTion will be applicable since it gives a clean separation between coding and non-coding sequences. However, a specific application might need a higher sensitivity at the cost of becoming less specific. If so, in that application a lower threshold should be considered. Conversely, if the application needs a higher specificity at the cost of losing some sensitivity, then a higher threshold (greater than 1.5) should be used.

TABLE 1

Percentage of Sequences that Fall Within Score Ranges using DiCTion

| Sequence Class | 0–1 | 1–1.5 | ≧1.5 | ≧1 | Avg. Length (bp) | Total (bp) |
|---|---|---|---|---|---|---|
| Full Length — Includes One Coding Region | 9.5% | 6.0% | 84.4% | 90.5% | 2043 | 880,809 |
| ORF — Coding | 3.5% | 3.5% | 93% | 96.5% | 1286 | 554,445 |
| 3' UTR — Non-coding | 91.1% | 7.4% | 1.5% | 8.9% | 638 | 256,997 |
| 5' UTR — Non-coding | 78.8% | 14.0% | 7.2% | 21.2% | 197 | 68,663 |
| Computer Generated Random Sequences — Non-Coding | 85.4% | 12.8% | 1.9% | 14.6% | 2000 | 862,000 |

Assuming that the threshold value is set to 1.5, a determination is made whether the score for the ORF is greater than or equal to 1.5 (step S.30). If the score for the ORF is equal to or greater than 1.5, then the ORF is flagged or marked in memory by the computing module to identify the ORF as being of interest or potentially corresponding to a protein-coding region (step S.40). If the score of the ORF is less than the threshold of 1.5, then it is determined whether there are additional ORFs in the sequence that have yet to be scored (step S.50). The steps of scoring and flagging appropriate ORFs continue until each identified ORF has been scored and analyzed (see FIG. 2).

After each of the ORFs have been scored and analyzed, a determination is made as to whether there is at least one ORF with a score that is greater than or equal to the threshold (i.e., greater than or equal to 1.5) (step S.60). If it is determined that all ORFs scored below the threshold, then the sequence may be predicted or identified as being non-coding (steps S.70). If, however, there is one or more ORFs that scored above the threshold, then the flagged ORF(s) are analyzed to identify the coding region(s) of the sequence (step S.80). If only one flagged ORF was identified, then the flagged ORF is identified as coding. If more than one flagged ORF exists, selection among them can be made on the basis of other criteria, such as length, EST coverage or protein homology, as indicated above. Of course, it is possible that more than one of the flagged ORFs will correspond to a protein-coding region. This can happen with frame shifts in a cDNA sequence or due to introns in genomic DNA. As such, the longest, flagged ORF can be identified or reported by the computing module as corresponding to a coding region. It is also possible for the computing module to identify or report the other flagged ORFs, which had a score above the predetermined threshold, to permit a researcher or end user to further analyze these ORFs and determine whether they also correspond to protein-coding regions.

As indicated above, the features and aspects of the present invention are not limited to the inspection of cDNA sequences. The processes and operations of FIG. 2, as well as FIG. 3 described below, may be modified to identify protein-coding regions in any RNA or genomic DNA sequence. In particular, by analyzing regions of a given sequence between pairs of termination codons or splice sites, instead of analyzing ORFs, coding regions within any genomic DNA sequence can be identified.

When determining the score of an ORF or any sequence region, the DiCTion function of the present invention may be utilized to examine the periodicity of each of the bases at a frequency of ⅓. Other cosine based functions or transformation functions may also be utilized. In order to provide a better understanding of the DiCTion function of the present invention, reference will now be made to FIG. 3. FIG. 3 illustrates the various processes and operations that may be performed to calculate the score of an ORF or sequence region using the DiCTion function.

The features and aspect of the exemplary flowchart of FIG. 3 may be performed as part of step S.20 in FIG. 2 for calculating the score of each ORF. Initially, a variable P, representing the index of the starting nucleotide of the ORF, is set to 1 (step S.100). Thereafter, binary streams are generated for each of the bases (α=A, C, G, T) for the length of the ORF starting from the first nucleotide to the end of the ORF (step S.110). As indicated above, each binary stream may be calculated based on the delta function ($U_\alpha(j)$), which is set to 1 or 0 depending on the presence or absence of the base (α) at each position, j in the sequence. For each binary stream represented by the delta function ($U_\alpha(j)$), the value is calculated in accordance with the following:

$$V_\alpha = \left| \sum_{j=1}^{N} U_\alpha(j)\cos(2\pi F j) \right|^2$$

As a result, a value $V_\alpha$ is calculated for each of the bases (step S.115). The calculated values for each of the bases ($V_A$, $V_C$, $V_G$, $V_T$) are then summed and multiplied by 1/N, where N is the length of the sequence. The result, $D(F)_P$ is then stored (step S.120).

As illustrated in FIG. 3, in order to calculate additional values, P is incremented by 1 (step S.125) and a determination is made as to whether P equals 4 (step S.130). If P equals 4, then values have been calculated for the length of the ORF assigning the three possible indices to the starting nucleotide of the ORF. As a result, additional computation is not necessary. If, however, P is not equal to 4, then logic flow loops back to calculate additional values, $D(F)_P$ for the next value of P (steps S.110–S.125). The value of P, of course, can be set to different values depending on the frequency that is being inspected. Thus, if a different frequency is evaluated (e.g., F=¼), then the value of P should be adjusted (e.g., P=5) accordingly to perform the proper number of logic flow loops in FIG. 3.

After $D(F)_P$ is calculated for the three indices, a determination is made as to which P provided the greatest value for $D(F)_P$. The value of P with the greatest value for $D(F)_P$ is set as the index for the ORF (step S.135). Further, the score for the ORF is set to the value of $D(F)_P$ at the index for the ORF (i.e., the value of P that provides the greatest value for $D(F)_P$).

In the exemplary embodiment of FIG. 3, the frequency F that is used to calculate the values $D(F)_P$ based on the DiCTion function is set to F=⅓. At a frequency F of ⅓, three distinct values can be obtained using the DiCTion function. Since the only difference between the three values is the index in the starting codon in the sequence, which is an arbitrary choice, these differences are immaterial. Therefore, as indicated above, all three values are calculated (for P=1, 2 and 3) and only the maximum is reported.

Cosine-based functions, such as the DiCTion function, are computationally intensive.

However, when the frequency F is fixed, there are only a small number of cosines to compute. For example, at the frequency F of ⅓, there are only three cosine values (i.e., −0.5, 0.0 and −0.5). All of the cosine calculations will cycle through these three values. Thus, the evaluation performed by the DiCTion function may be optimized greatly by not resorting to any computational calls to the cosine function during operation. Instead, the three cosine values may be applied directly as part of the calculation with the DiCTion function depending on the position, j in the sequence. For other values of F, a look-up table could be constructed to optimize the implementation by eliminating putative cosine computations.

In order to demonstrate the accuracy of the present invention, two examples will now be discussed. In the first example, the positive database Bullet Train (BT) is utilized. Bullet Train includes sequences which contain a coding ORF. In the second example, the negative database Control DB is utilized that includes sequences that do not contain a coding ORF. The Bullet Train and Control DB databases are described in greater detail above in connection with Table 1.

In the first example, a score was calculated for every ORF in every sequence of Bullet Train, using the DiCTion function and other features of the present invention. In calculating this score, the frequency F was set to ⅓ and the threshold was set to 1.5. If a given sequence had an ORF whose score was greater than or equal to 1.5, the ORF was identified or predicted as corresponding to a coding region. Further, ORFs having a score less than 1.5, were identified as non-coding. As indicated in Table 2 below, applying this analysis to the Bullet Train database, 382 of the 405 Bullet Train sequences were correctly predicted to be coding. In other words, 94.3% of the actual coding regions were accurately identified through the features of the invention. Applying a similar analysis to the sequences in the Control DB database, approximately 6.5% of the 3' UTR and 11.1% of the 5' UTR sequences were predicted as being coding.

TABLE 2

Performance of DiCTion

| Sequence Data Type | Number of Sequences | | Coding Predicted Percent |
|---|---|---|---|
| | Total | Score ≧1.5 | |
| Bullet Train | 405 | 382 | 94.3% |
| 3' UTR—Control DB | 6707 | 433 | 6.5% |
| 5' UTR—Control DB | 1469 | 163 | 11.1% |

Ideally, all sequences in Bullet Train (BT) and none of the sequences in the UTRs of the Control DB database should be predicted to be coding. Based on these two examples, the present invention provides a false negative rate of approximately 5.7% and false positive rate of approximately 6.5 to 11%. In summary, there were 382 true positives (TP), 23 false negatives (FN), 596 false positives (FP), and 7,580 true negatives (TN). This provides a sensitivity (defined as TP/(TP+FN)) of the invention of approximately 94.3%, and provides a specificity (defined as TN/(TN+FP)) of approximately 92.7%. To the knowledge of the inventors, this the best discrimination between coding and non-coding sequences ever achieved.

False negatives produced by using the DiCTion function and features of the invention are caused by two main reasons. First, the ORFs may be too short to provide reliable results. Here, the reason is not so much that the pattern is absent, but that it is too subtle and the length of the ORF is simply not sufficient to build the score up to 1.5. Second, a shifting-index scenario may lower the score. For example, portions of a long coding region may individually score above the threshold but with different indices. Suppose three portions of a coding region will individually score well but that the first part has an index of 1, the second part has an index of 3, and the third part has an index of 2. An index of 1 means that there is some repetitiveness with the DNA sequence which causes a base to prefer position I of the codon (or triplet). Similarly for index 2 and 3. Thus, when the entire region is evaluated with all 3 indices mixed up, preference for any position of the codon is obliterated or significantly weakened. Here too, the reason for the false negative is not so much that the pattern is absent, but that the phase of the pattern keeps changing.

To further illustrate the advantages and accuracy of the present invention, additional examples will now be discussed, by comparing the results of the present invention to past approaches, such as GRAIL. Below, Table 3 provides a comparison of the performance of the present invention, as measured against the Bullet Train and Control DB databases, with the reported results of past approaches (such as GRAIL and GeneScan) and ORF Lookup (an approach, disclosed in greater detail below, in which ORFs above a predetermined length are determined to be coding). In comparing the performance results indicated in Table 3, it is important to remember that the performance results of the present invention are based on an analysis of cDNA sequences, whereas the reported performances for most methods of detecting coding regions typically relate to genomic sequences. Therefore, a direct comparison of the results of the present invention with the reported results of past approaches can be inappropriate. Nonetheless, as indicated in Table 3, no other previous method or technique has both a sensitivity and specificity that is greater than 90%.

TABLE 3

Indirect Comparison to Published Results of Different Methods

| Method | Sensitivity | Specificity | Type | Reference |
|---|---|---|---|---|
| DiCTion | 94.3% | 92.7% | cDNA | Present Invention |
| GRAIL | 90% | Not available | genomic DNA | Uberbacher & Mural (1991) |
| GeneScan | 66% | 60% | genomic DNA | Tiwari et al. (1997) |
| Lengthen-shuffle FT | 68–89% | 70–80% | genomic DNA | Yan et al. (1998) |
| ORF Lookup | 100% | 75–80% | cDNA | Present Invention |

Table 4 indicates the results of a more direct comparison of the capabilities of the present invention with that of a prior technique, GRAIL and with that of ORF Lookup. Version 1.0 of GRAIL (UBERBACHER & MURAL, 1991) is typically used on genomic sequences. However, GRAIL can also be applied to cDNA sequences. As such, in this example, the GRAIL method has been applied to the sequences in Bullet Train, as well as those in the Control DB database. The results of applying GRAIL and ORF Lookup to Bullet Train and Control DB are indicated below in Table 4.

Finding a relatively long ORF in a cDNA sequence is itself a good indicator of coding potential. In order to illustrate how much of the present invention is due to simply finding ORFs, in Tables 3 and 4 a simple ORF Lookup prediction approach has also been applied to Bullet Train and Control DB, as indicated above. In the ORF Lookup prediction, any sequence that has at least one ORF longer than 80 codons (i.e., 240 nucleotides) is predicted to be coding.

TABLE 4

Direct Comparison to GRAIL and ORF Lookup

| Type | Total Number | DiCTion | | GRAIL | | ORF Lookup | |
|---|---|---|---|---|---|---|---|
| | | Positive | Percent | Positive | Percent | Positive | Percent |
| Bullet Train | 405 | 382 | 94.3% | 394 | 97.3% | 405 | 100% |
| 3' UTR | 6707 | 433 | 6.5% | 1662 | 24.8% | 1644 | 24.5% |
| 5' UTR | 1469 | 163 | 11.1% | 299 | 20.4% | 304 | 20.7% |

As indicated in Table 4, both GRAIL and ORF Lookup are slightly more sensitive than the present invention. In fact, ORF Lookup correctly predicts every sequence in Bullet Train to be coding. This is because none of the sequences in Bullet Train has an ORF smaller than the 80-codon cutoff. However, both GRAIL and ORF Lookup have substantially lower specificity. In fact, GRAIL and ORF Lookup predict 20 to 25% of UTR sequences to be coding (i.e., they have a high false positive rate). In most high-throughput sequencing efforts, this difference in specificity is of crucial importance because a majority of sequences examined will turn out to be non-coding.

As indicated above, the analysis of any given sequence is performed by inspecting the periodicity of each of the bases at a frequency of ⅓. While peaks at frequencies other than ⅓ (i.e., noise) may be comparable to the signal (peak at ⅓), the overall prediction by the present invention is still very reliable. As such, in the signal analysis performed by the present invention, it is advantageous to ignore noise and concentrate instead on the absolute value of the signal. From the standpoint of the physics of signal analysis, ignoring noise may seem to be a mistake, but in this biological context it make sense. A DNA sequence may have periodicities at many different frequencies because of special characteristics of the gene and the protein it encodes. The peak at ⅓ occurs due to the fact that a given sequence is coding, a property shared by all genes. Thus, in measuring only coding capacity, it is acceptable to ignore peaks at other frequencies.

The features of the present invention are well suited for the analysis of cDNAs, particularly in a high-throughput pipeline because the calculation is very fast and reliable. In such a case, sensitivity and specificity both need to be high because limiting most false positives (specificity) is at least as important as catching most true positives (sensitivity). As indicated above in Tables 3 and 4, past approaches and techniques usually have lower specificity than the present invention. Given that database artifacts and other non-coding regions are common in many high-throughput efforts, using a low-specificity method will lead to a lot of wasted effort, time and money.

The goals of most of the past approaches and methods is to identify exons in a genomic sequence. This typically means the method needs to pinpoint where an exon begins and ends. Therefore, all of the past approaches use a sliding window for calculation. The theory is that when the window crosses into a coding region, the "coding property" that is being measured will show a significant increase. However, due to this assumption, the size of the sliding window has to be maintained relatively small. Making it too big will dramatically lower the precision of predicting exon boundaries. When the window is small, the coding property being calculated (like periodicity) can take on spurious values. Short stretches of non-coding sequences can exhibit properties of coding sequences and vice versa.

When dealing with cDNAs with the present invention, however, identifying the borders of the coding region is not as big a problem because the ORF has to begin with an initiation codon and end in a termination codon. The present invention uses this basic piece of information and performs calculations on open reading frames (ORFs) instead of on sliding windows. There are three advantages of this approach compared to the sliding window approach. First, the sequence of an entire putative coding region is used in the calculation, reducing the risk of misprediction due to short stretches of sequence showing anomalous characteristics. Second, genomic repeats which are very common in the untranslated regions of cDNAs are not mispredicted to be coding if they do not fall within ORFs of substantial size. Furthermore, DiCTion correctly predicts non-simple repeats to be non-coding even if they do appear in ORFs. Third, the number of ORFs in a given sequence is substantially less than the number of windows that are possible in it. Therefore, there is a gain in computational speed.

Although methods consistent with the present invention have been disclosed for processing cDNA sequences, such methods are not restricted to cDNA sequences. They are adaptable for analyzing any genomic DNA sequence and for performing exon detection. Such adaptations may be achieved based on the principle that adding non-coding sequence to an exon reduces its DiCTion score on average (see, for example, FIG. 6). Another possible approach is analogous to the ORF approach for cDNAs. In this approach, canonical intron donor and intron acceptor sites are identified within a sequence, and the sequence region between the donor and acceptor sites is analyzed in place of the ORF, in accordance with a similar process to that of FIGS. 2 and 3.

Figure 4A:
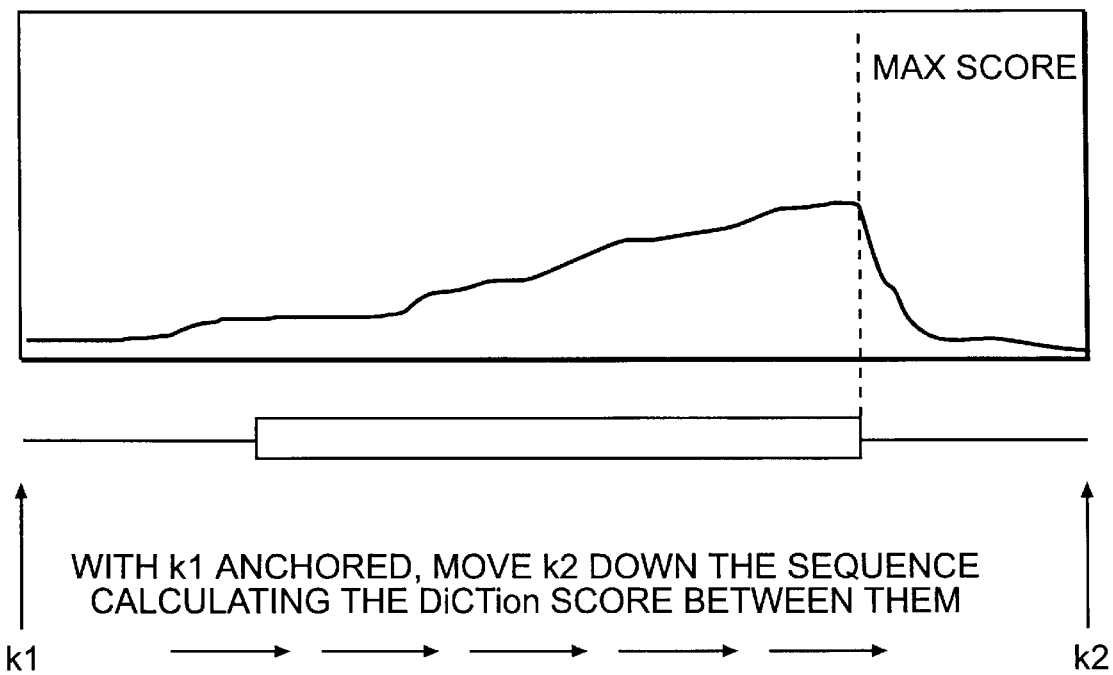
FIG. 4 illustrates an exemplary process for detecting borders within a sequence, in a manner consistent with the present invention.
Figure 4B:
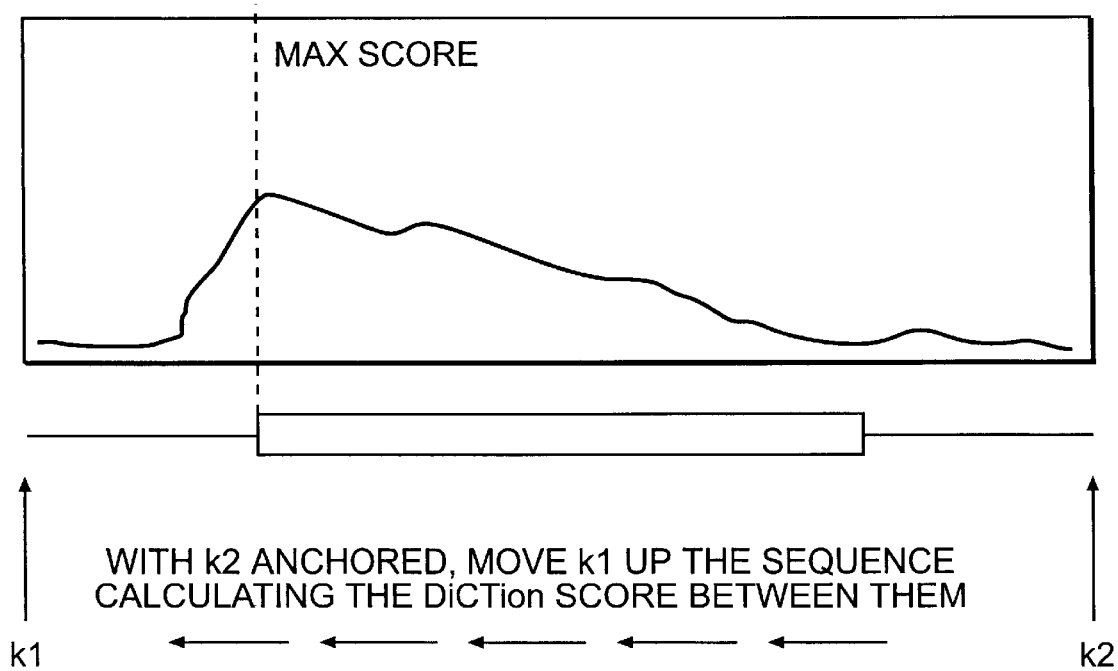
Figure 5A:
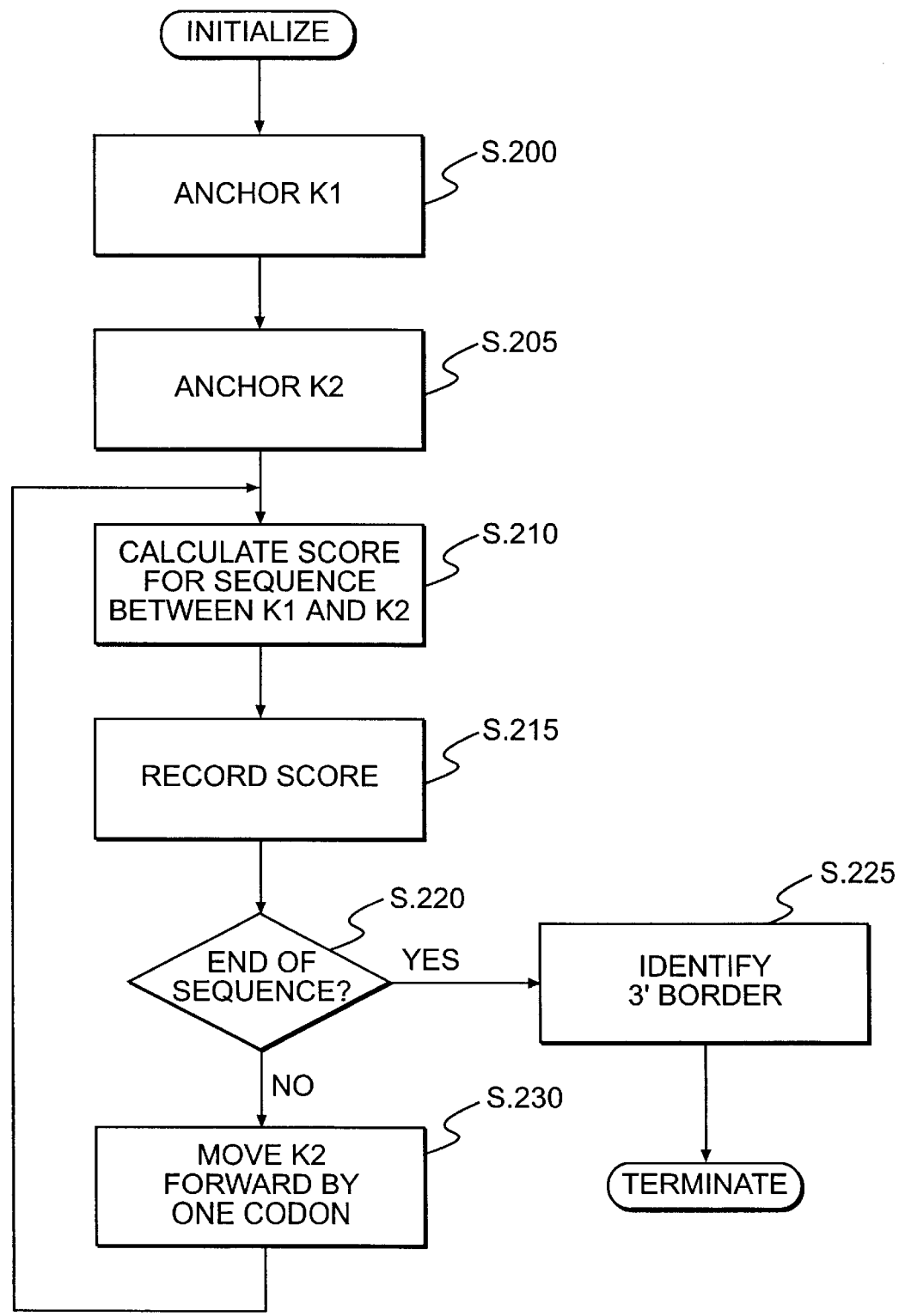
FIGS. 5A and 5B are exemplary flowcharts of a process for detecting borders of a coding region in a nucleic acid sequence, in a manner consistent with the present invention.
Figure 5B:
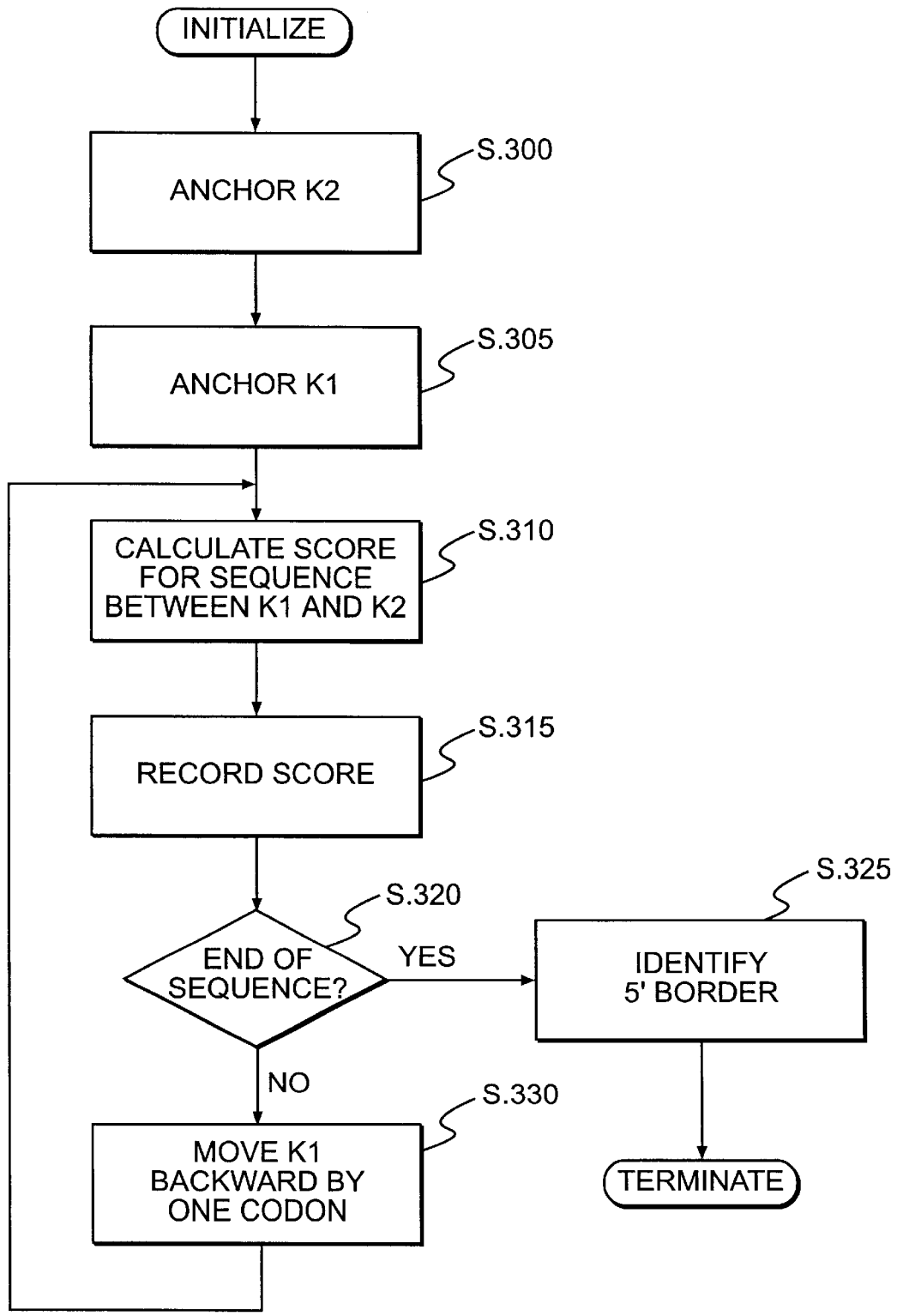

As indicated above, the features of the present invention may be utilized for the purposes of border detection. FIGS. 4, 5A, and 5B illustrate a process for detecting borders in accordance with an embodiment of the present invention. This feature may be utilized to determine the borders (e.g., the 5' border and the 3' border) as part of an overall process for identifying coding regions in a sequence, or as part of a process for detecting the full length of an identified coding region.

Genomic sequences containing introns (non-coding) and exons (coding). In the ideal case, the score computed with, for example, the DiCTion function of the present invention will be maximal when the entire coding sequence (from 5' border to 3' border of the coding sequence, e.g., an exon) is tested. Consider, for example, the case of a coding region flanked on either side by non-coding regions where it is unknown where (or even if) a coding region begins and ends. Using the DiCTion function and the use of two arbitrary borders or anchors (k1 and k2), it is possible to predict the borders of the coding region by calculating the DiCTion score for the sequence between the anchors and independently moving each of the anchors until the maximum DiCTion score is determined. FIG. 4 illustrates this principle of the invention in graph form. In general, using this aspect of the invention, two arbitrary borders or anchors (k1 and k2) are placed along the sequence. For example, the first anchor k1 may be placed at the start of the sequence with the anchor k2 placed at some minimal threshold distance (e.g., 50 nucleotides) away from the first anchor k1. Thereafter, the DiCTion score for the sequence between the two borders is calculated. As the k2 anchor is moved away from the k1 anchor, codon by codon, the score for the region between the two anchors is recalculated. As the k2 anchor enters the coding region, the DiCTion score will begin to rise until it reaches a maximum. This maximum corresponds to the 3' border of the coding region. A similar method is then applied to the sequence to determine the 5' border of the coding region, by anchoring the k2 anchor at the 3' end of the sequence and moving the k1 anchor away from k2 until the maximum is again reached.

FIGS. 5A and 5B illustrate exemplary flowcharts of the steps for identifying or predicting the 3' border and the 5' border in the sequence. To identify the 3' border, as illustrated in FIG. 5A, the k1 anchor is positioned along the sequence (step S.200) followed by positioning the k2 anchor on the sequence (step S.205). In this regard, the k1 anchor may be set at the start of the given sequence with the k2 anchor set a minimal threshold distance (e.g., 50 nucleotides) away from k1. Following the positioning of the anchors k1 and k2, the score for the region of the sequence between k1 and k2 is calculated (step S.210). This score may be calculated in accordance with the DiCTion function and the various features and operations disclosed above with respect to FIGS. 2 and 3. The score is then recorded for the current positions of k1 and k2 (step S.215). This process is repeated as the anchor k2 is moved away from k1 one codon at a time until the end of the sequence is reached.

In particular, as illustrated in FIG. 5A, after each score is recorded, a determination is made whether the end of the sequence has been reached (step S.220). When it is determined that the end of the sequence has been reached, the 3' border is identified (step S.225) by determining the position of k2 that yields the maximum score between k1 and k2. Otherwise, k2 is moved forward or down along the sequence by one codon (step S.230) and additional calculations of the score are made until the end of the sequence is reached. FIG. 5B is an exemplary flowchart of a process for determining the location of the 5' border in a sequence. The overall process disclosed in FIG. 5B is similar to that described above for FIG. 5A. That is, the arbitrary anchors k1 and k2 are first positioned along the coding region of the sequence. If the 3' border has been determined, then the k2 anchor is positioned at a location corresponding to the 3' border in the sequence (step S.300). The anchor k1 is then positioned at some minimum distance away from the k2 anchor (step S.305). By way of a non-limiting example, the k1 anchor may be set at a position that is 50 nucleotides away from the k2 anchor. After k1 and k2 are positioned along the sequence, the score of the sequence region between k1 and k2 is calculated (step S.310). This score may be calculated using the DiCTion function and features of the invention described in reference to FIGS. 2 and 3. The score for each position of k1 and k2 is recorded (step S.315) until the end of the sequence is reached.

As illustrated in FIG. 5B, when the end of the sequence is reached (step S.320), the 5' border in the sequence is identified (step S.325). In this regard, the position of k1 that yields the maximum score between k1 and k2 is identified as the 5' border of the coding region. If the end of the sequence has not been reached, then k1 is moved backward or up the sequence away from k2 by one codon (step S.330). Thereafter, the score of the sequence region between k1 and k2 is recalculated until the end of the sequence is reached.

Figure 6:
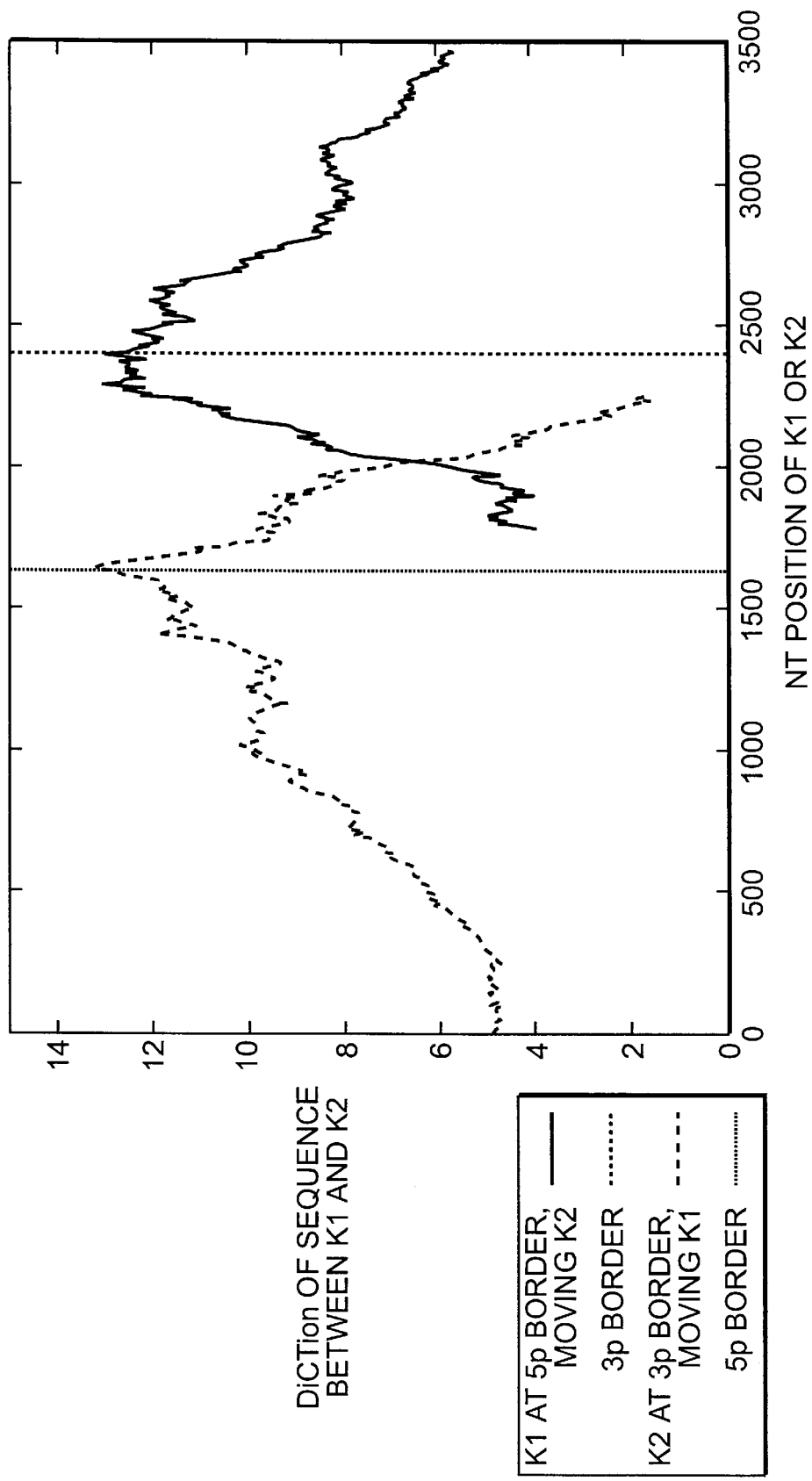
FIG. 6 illustrates an exemplary process of analyzing human cMYC gene to identify intron and exon borders, in a manner consistent with the present invention.

The border detection techniques of the present invention may be applied to identify exon borders of various genes. For example, the border detection method of the invention was tested on a portion of the c-MYC gene which has a intronexonintron structure. As illustrated in FIG. 6, the border detection technique of the present invention successfully identified the location of the 5' and 3' exon borders of the exon contained within the sequence. That is, in the example of FIG. 6, the DiCTion score between k1 and k2 was a maximum for both nucleotides (NT) positions in the sequence corresponding to the borders.

The principles and aspects of the present invention may be utilized for a wide array of applications. As described above, the present invention provides a powerful technique for identifying coding regions within any genomic DNA sequence. The present invention also provides useful computational tools for detecting characteristics and gathering information from an unknown sequence, such as the location of exon borders. The features of the invention may also be used or combined to provide other useful applications, such as those described below.

One useful application of the present invention is for the detection and weeding out of non-messenger RNAs in a sequence. A portion of cDNA sequences in any cDNA library will be non-coding. This might happen because the reverse transcriptase, used to prepare the library or database, primed off of genomic DNA or hetero-nuclear RNA. The presence of non-coding regions may also occur when the reverse transcriptase priming did not go up to the 5' border end of an mRNA and, therefore, the resulting cDNA might only contain the 3' untranslated portion of the gene. Therefore, a major problem in any high-throughput effort is identifying and eliminating cDNAs that are not representative of real coding sequences.

The DiCTion function and coding region prediction features of the present invention are well suited to solve this problem. As explained above, the features of the present invention may be utilized to distinguish between coding and non-coding sequences. This process generally involves the following main steps: (i) identifying all open reading frames (ORF) in the sequence; (ii) analyzing the periodicity and calculating the score of every identified ORF; and (iii) identifying any ORF with a score that is above a predetermined threshold to be coding. This procedure will identify coding sequence while eliminating non-coding sequences and provide an accuracy of approximately 95%.

Another useful application of the invention is for determining whether a particular cDNA sequence is full length. Depending on the source of the sequence data, a particular cDNA sequence may or may not include the true 5' and/or 3' borders. For example, in a cDNA database or library construction, the reverse transcriptase priming can stop before reaching the true 5' end of a gene. In these cases, the constructed cDNA will not represent the full length mRNA, but will instead be truncated at the 5' end. The features of the present invention can be utilized to determine whether a cDNA sequence or clone is full length.

Figure 7:
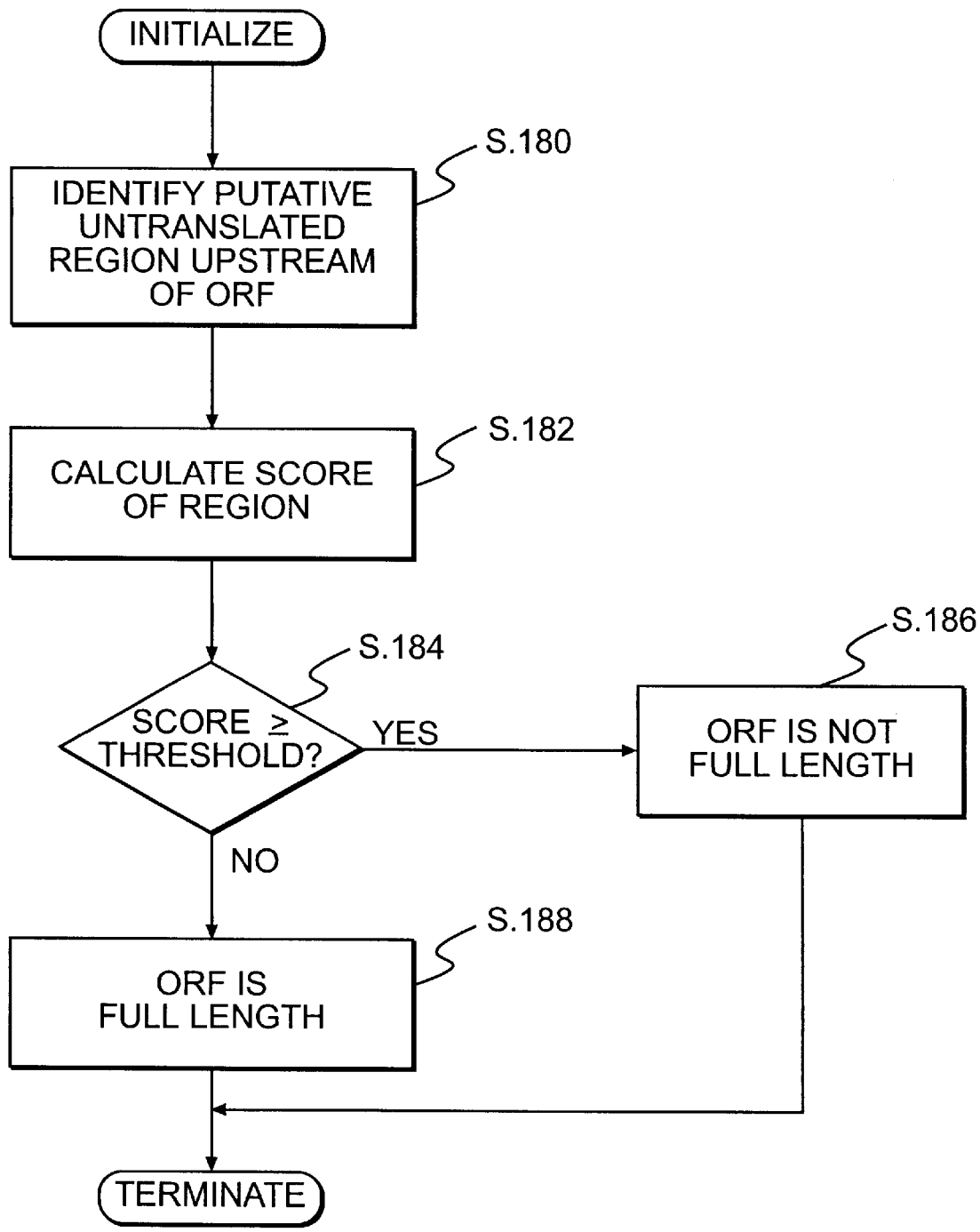
FIGS. 7 and 8 are exemplary flowcharts of processes to determine whether a cDNA sequence is full length, in a manner consistent with the present invention.

FIG. 7 illustrates an exemplary flowchart of various processes and operations that may be carried out, in accordance with an embodiment of the present invention, to determine whether the ORF or sequence region is full length. The features and aspects of FIG. 7 can be utilized to determine whether a putatively identified ORF or sequence region predicted to be coding includes the true 5' border or whether it is truncated. In the case of a cDNA sequence, an ORF can be predicted to be coding by applying the principles and features of the present invention (such as FIGS.2 and 3). Therefore, the features and aspects of FIG. 7 may be combined with other aspects of the present invention as part of an overall analysis of genomic sequence data.

As illustrated in FIG. 7, after identifying the ORF in the cDNA sequence, the region of the sequence that is upstream of the ORF is identified (step S.180). The upstream region may be identified as corresponding to the portion of the sequence that exists between the initiation codon of the ORF up to the start of the sequence (upstream of the initiation codon).

The score of the upstream region is then calculated (step S.182). In this regard, the discrete cosine transformation (DiCTion) function of the present invention, as well as the features and aspect of FIG. 3, may be applied to determine the score of the upstream region. Thereafter, a determination is made as to whether the score for the upstream region is greater than or equal to a predetermined threshold (step S.184). As indicated above, this threshold may correspond to a value of 1.0 or 1.5. If the score for the upstream region is greater than or equal to the predetermined threshold, then the ORF may be predicted as not being full length (step S.186). In such a case, the exact location of the 5' border may be analyzed and determined using the features of the present invention, including the border detection techniques of the invention disclosed herein. If the 5' border is not present within the cDNA sequence, then the cDNA clone itself is predicted not to be full length. If, however, the score of the upstream region is less than the predetermined threshold, then the ORF may be identified as being full length (step S.188).

The features of FIG. 7 are not limited to determining whether an ORF of a cDNA sequence is full length. That is, the features and aspects of FIG. 7 can be also be applied to determine whether other predetermined regions (e.g., SSS regions or regions between splice sites) of a sequence are full length. By analyzing the portion of the sequence that is upstream of the predetermined region, consistent with the principles of FIG. 7, it is possible to determine whether the predetermined region is full length.

Figure 8:
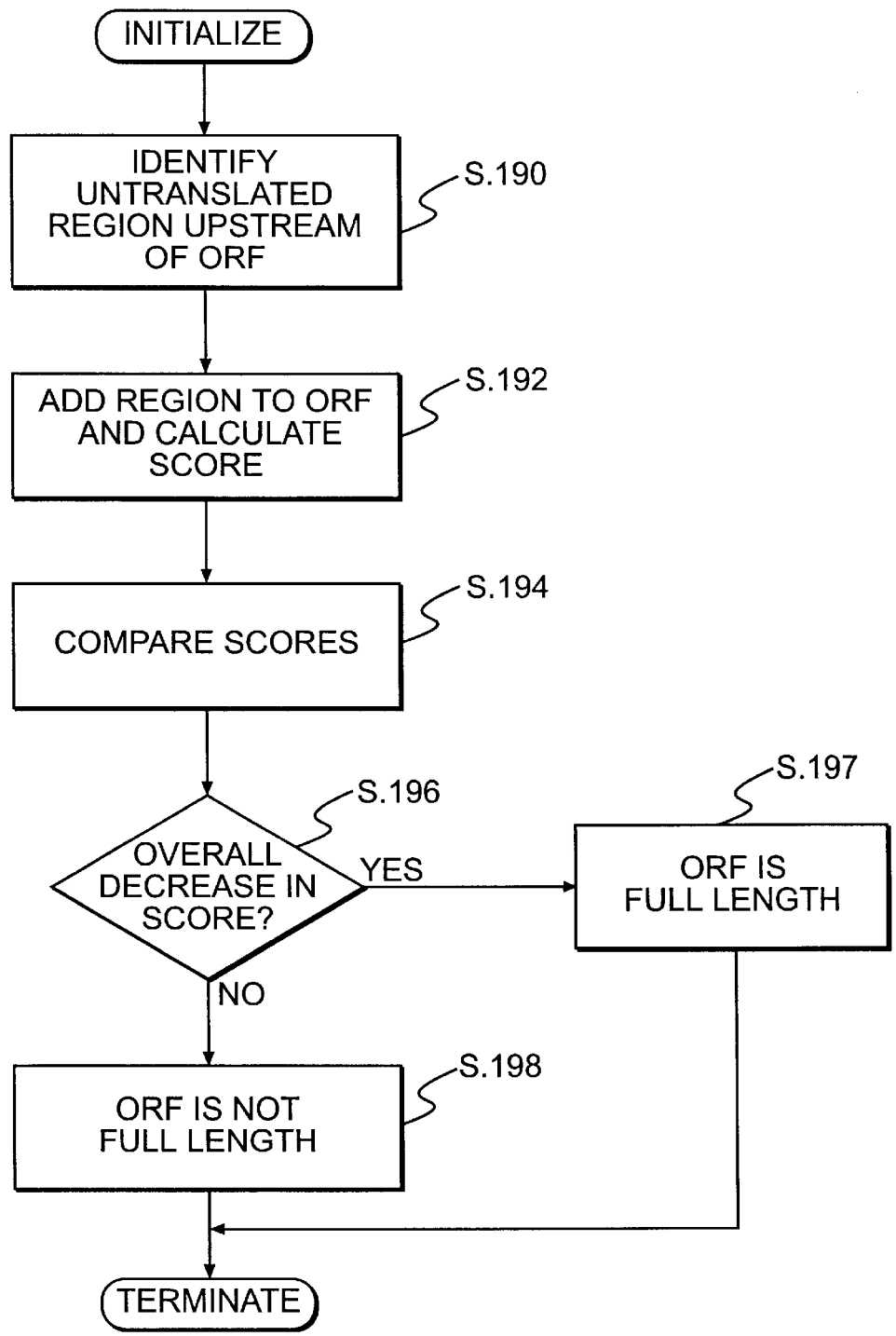

FIG. 8 illustrates, in accordance with another embodiment of the present invention, the various processes and operations that may be performed in order to detect whether a ORF of a cDNA sequence is full length. In the embodiment of FIG. 8, the score of the upstream 5' region combined with the ORF is analyzed, instead of analyzing simply the score of the 5' region. In particular, after scoring and putatively identifying the ORF in the cDNA sequence, the 5' region upstream of the ORF is identified (step S.190). Once again, the upstream region may be identified or determined by locating the initiation codon of the ORF and the first codon of the sequence. After identifying the upstream 5' region, this region is added to the ORF and a score is calculated for the combined portion of the cDNA sequence (step S.192). The DiCTion function of the present invention, as well as the features and aspects of FIG. 3, can be utilized to determine the score of the combined region in the sequence.

As further illustrated in FIG. 8, the score of the combined region is compared with the score of the putatively identified ORF (step S.194). A determination is then made as to whether there has been an overall decrease in the score (step S.196). That is, a determination is made whether the score of the ORF is greater than the score of the ORF combined with the upstream 5' region. If there is an overall decrease in the score, then the ORF is determined to be full length (step S.197). If, however, there is no overall decrease in the score when the upstream region is added to the ORF, then the ORF is determined not to be full length (step S.198). In the latter case, the exact location of the 5' border may be determined by applying the border detection techniques of the invention to the identified ORF in the cDNA sequence. Once again, if the 5' border is not within the cDNA sequence, the cDNA clone itself is predicted to be not full length.

In the embodiments of FIGS. 7 and 8, the features of the invention have been described with reference to analyzing the upstream 5' region. The features of these embodiments are, therefore, helpful in determining whether the true 5' border is included in the sequence. The principles and features of the present invention, however, are not limited to such applications and can also be utilized to determine whether the true 3' end of a gene is present in the sequence. That is, by analyzing a downstream 3' region, the embodiments of FIGS. 7 and 8 may be modified to determine whether the putatively identified ORF is full length. In such a case, the downstream 3' region may be identified by determining the portion of the sequence between the termination codon of the ORF and the next start codon or the end of the sequence.

Sequencing a large number cDNA clones to identify the interesting ones is the main idea behind any high-throughput analysis. Due to the large number of sequences that need to be analyzed, sequencing errors may arise. One such error is frame shifts which may occur due to insertions and/or deletions. Frame shifts may cause a single long ORF to be split into two regions in a sequence (such as an ORF and a stop-stop stretch). Using the features of the present invention, the presence of frame shifts can be identified in an automated fashion through the use of a computing module or platform, such as that illustrated in FIG. 1.

Figure 9:
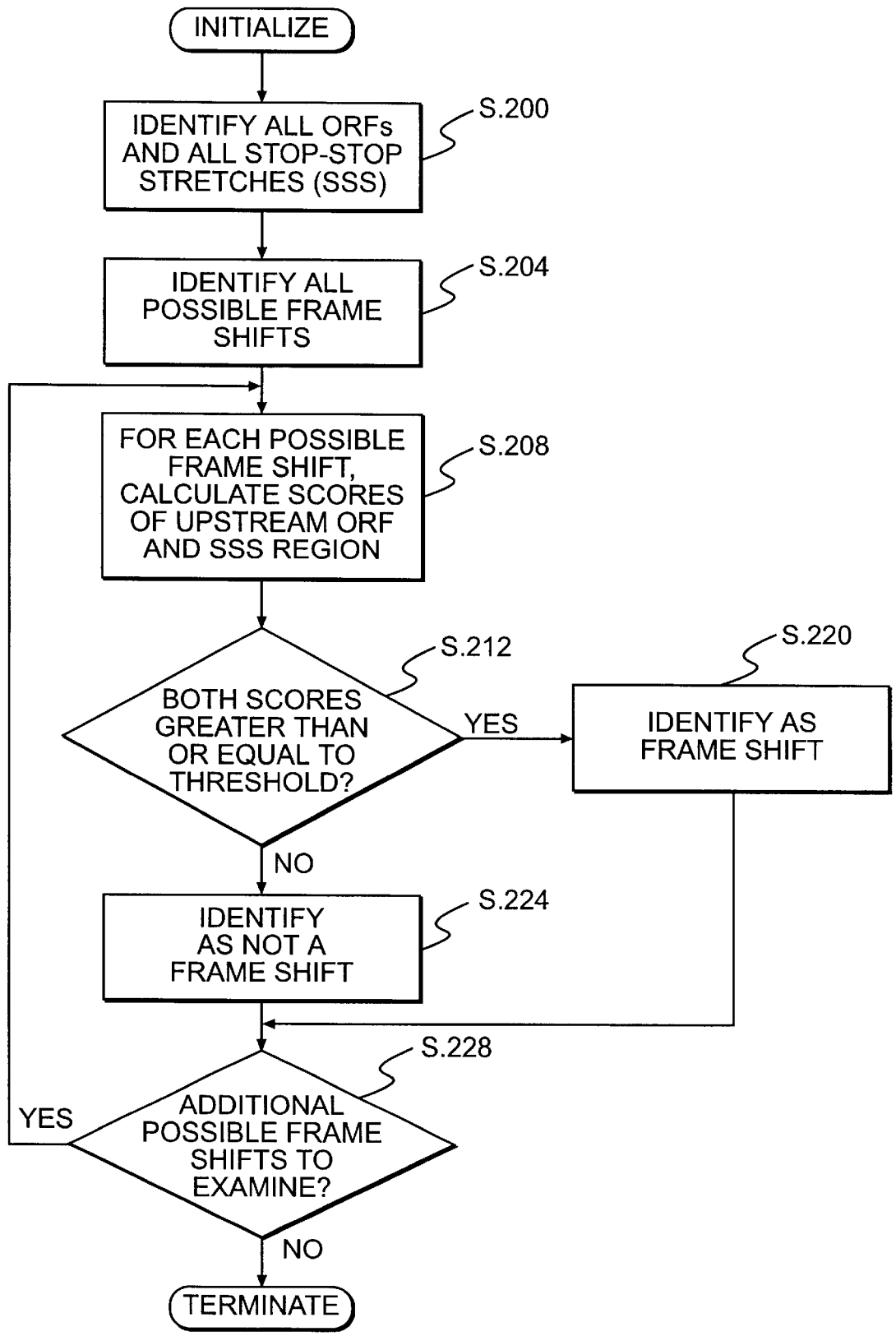
FIG. 9 is a exemplary flowchart of a process to identify frame shifts, in a manner consistent with the present invention.

In accordance with an aspect of the present invention, FIG. 9 illustrates an exemplary flowchart of the various processes and operations for identifying frame shifts in a cDNA sequence. As illustrated in FIG. 9, all of the ORFs and stop-stop stretches (SSS) in the sequence are first identified (step S.200). Each ORF may be identified by determining the location of an initiation codon and a downstream termination codon that is in-frame. Each SSS region can be identified in a sequence by locating pairs of termination codons.

After identifying all ORFs and SSS regions, each possible frame shift in the sequence is identified (step S.204). The identification of a possible frame shift can be performed by comparing all of the identified ORFs and SSS regions, and identifying overlaps occurring between ORFs or between an ORF and an SSS region. For example, a possible frame shift may be identified based on the presence of an ORF that overlaps in position in the sequence with a SSS region.

For each possible frame shift identified, a score is calculated for the upstream ORF as well as for the overlapping SSS region (step S.208). The DiCTion function and other features and aspects of the present invention can be utilized to calculate the scores of both the ORF and the SSS region. After the scores are calculated, a determination is made as to whether both scores are above a predetermined threshold (step S.212). As described above, this threshold may be set to 1.0 or 1.5. If both scores are above the predetermined threshold, then a frame shift is determined to be present (step S.220). If, however, both scores are not greater than or equal to the predetermined threshold, then the identified possible frame shift is also determined not to be a frame shift (step S.224).

Following steps S.220 and S.224 in FIG. 9, a determination is made whether additional possible frame shifts are present that need to be examined (step S.228-No). If there are additional possible frame shifts to examine, then logic flow recedes back to step S.208 to perform additional analysis of the overlapping ORFs and SSS regions.

If those scores are greater than or equal to the predetermined threshold (step S.212), then a frame shift is determined to be present (step S.220) for the identified overlapping ORF and SSS region. Thereafter, if there are no more possible frame shifts to examine (step S.228), then the process terminates.

Figure 10:
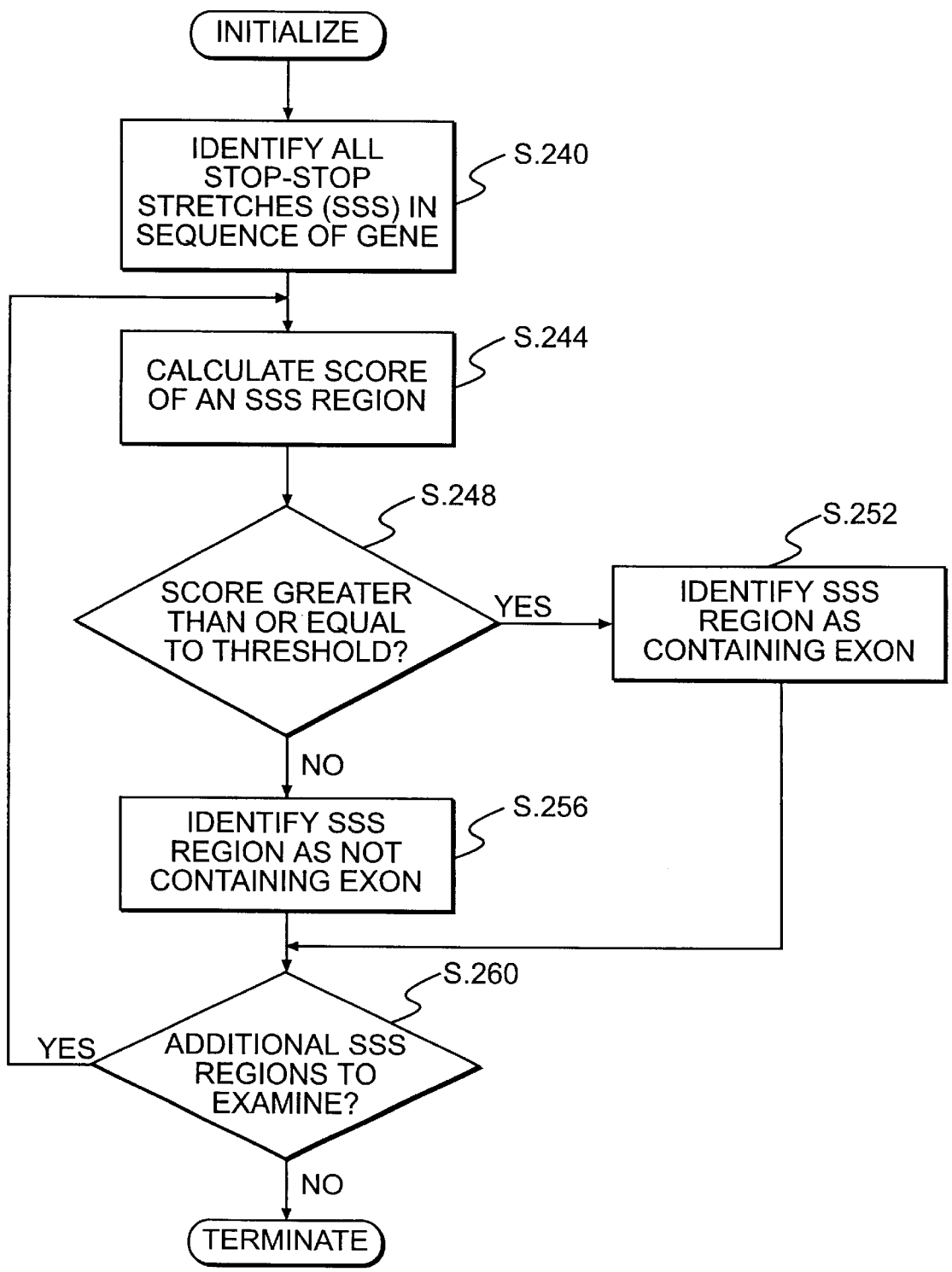
FIG. 10 illustrates an exemplary flowchart for performing a coarse analysis of a gene, in a manner consistent with the present invention.
Figure 11:
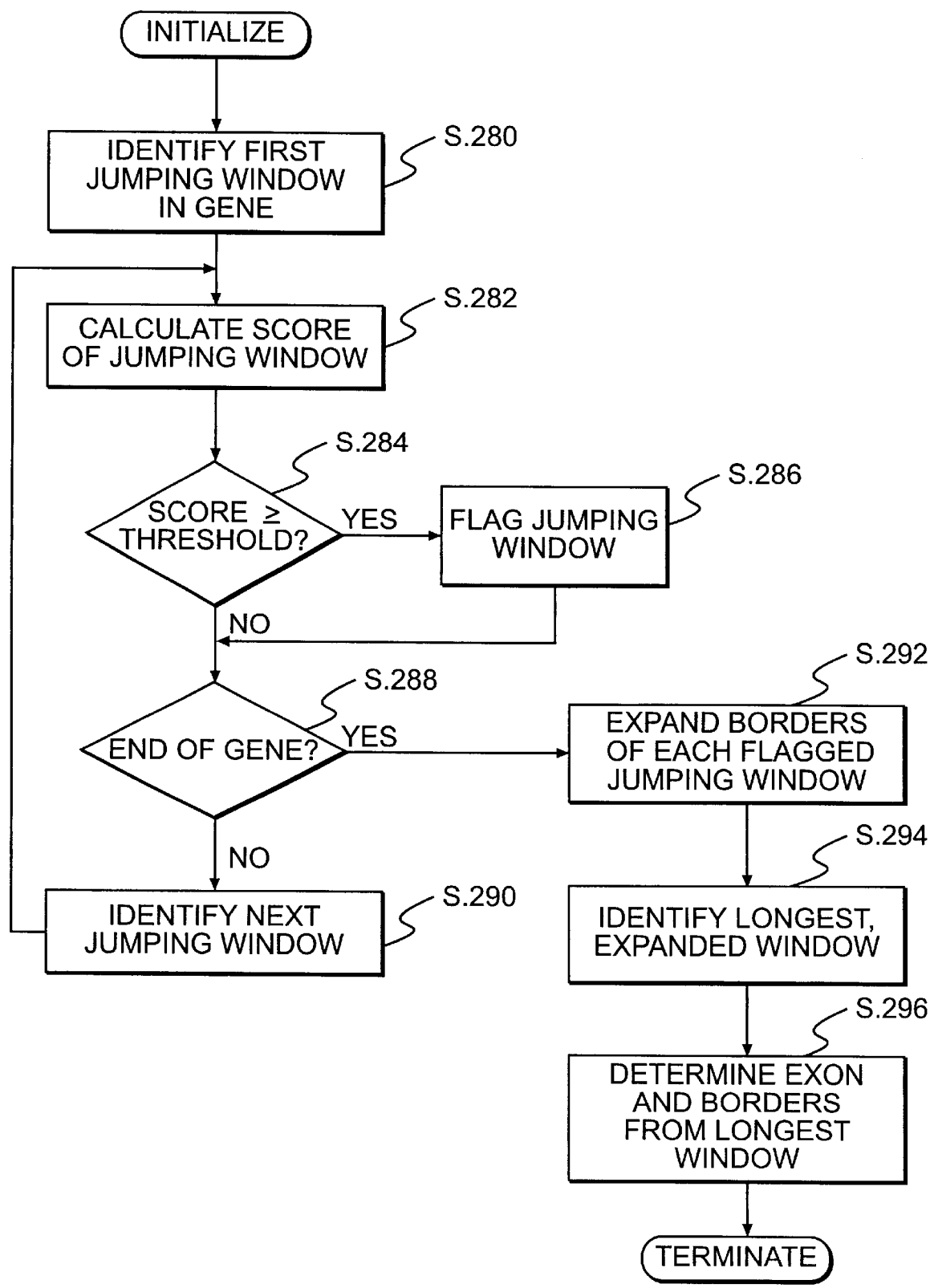
FIG. 11 is an exemplary flowchart of a process for performing a fine analysis of a gene using a grow technique, in a manner consistent with the present invention.
Figure 12:
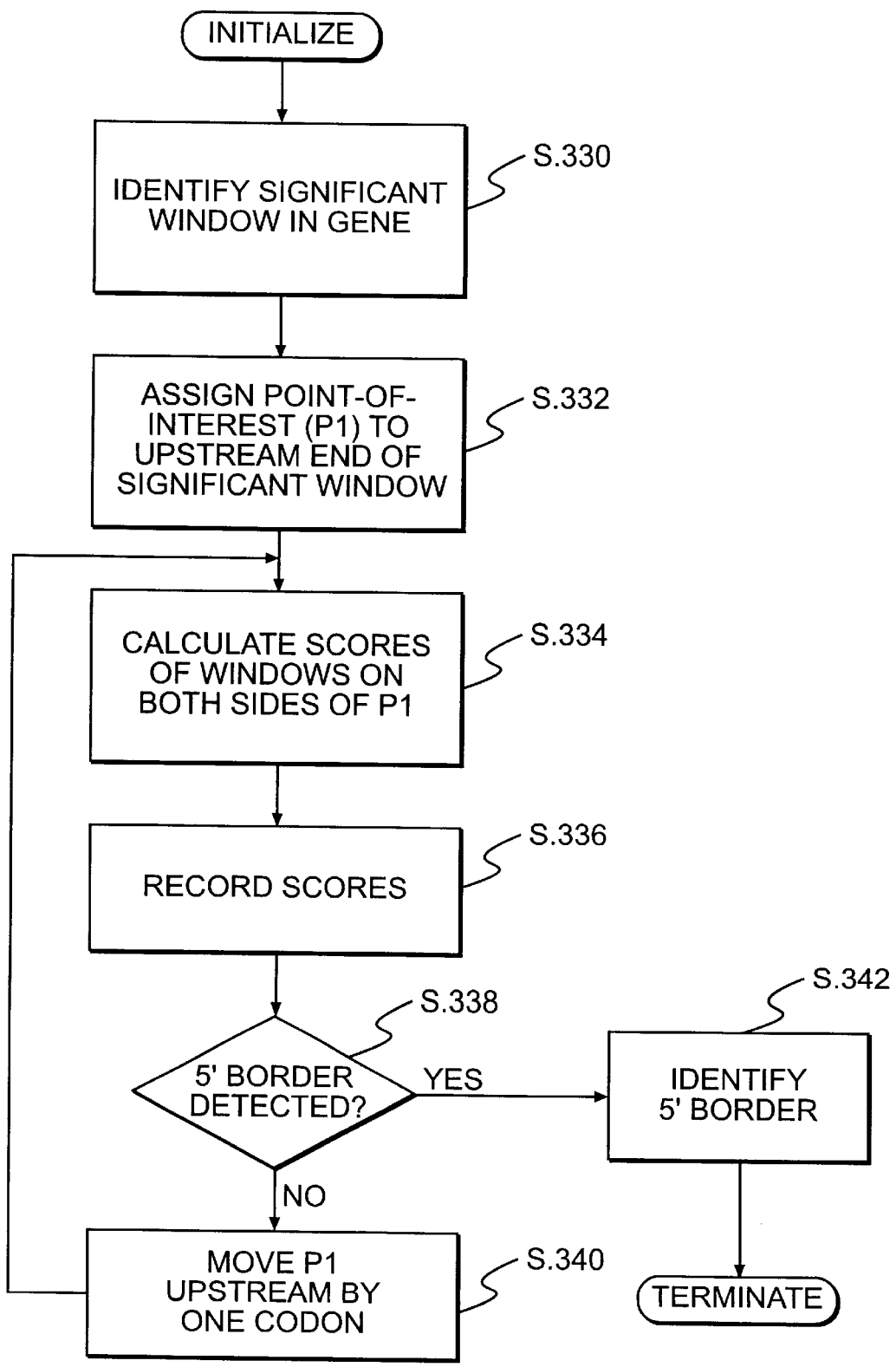
FIGS. 12 and 13 are exemplary flowcharts of processes for performing a fine analysis of a gene using an end-score technique, in a manner consistent with the present invention.
Figure 13:
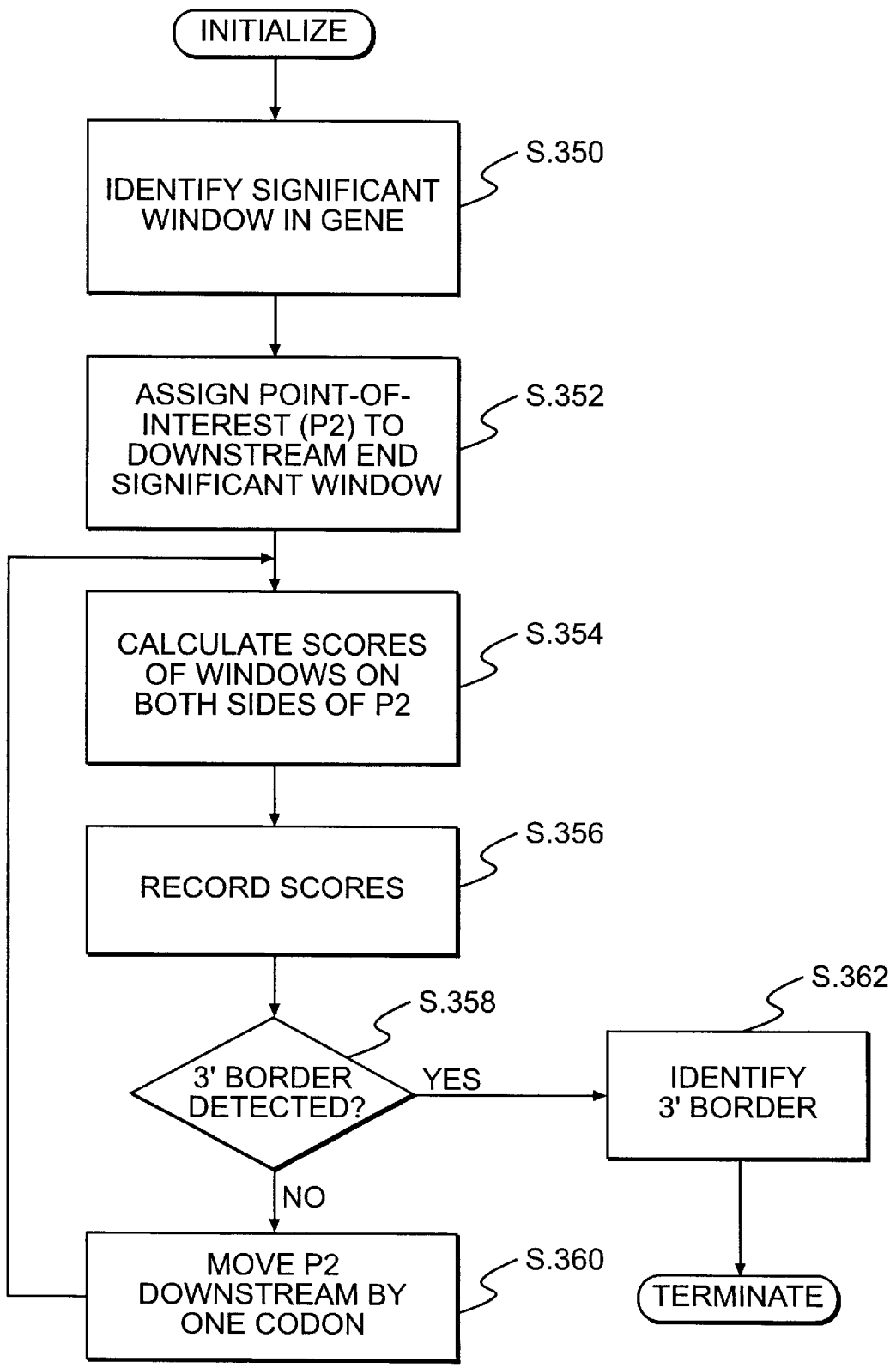

Once the sequence of a gene is known, the features of the present invention are ideally suited for the analysis required to determine the positions of the coding regions (exons), as well as the true ends or borders of a coding region or exon. In accordance with an additional aspect of the present invention, the features of the invention may be adapted to analyze genes at a coarse level or fine level of analysis. FIG. 10 illustrates an exemplary embodiment for performing a coarse analysis of gene, and FIGS. 11, 12, and 13 illustrate exemplary embodiments for performing a fine level analysis of genes.

The approximate positions of exons or coding regions within genes can be determined using the DiCTion function and features of the present invention. FIG. 10 is an exemplary flowchart of the various processes and operations that may be performed for identifying stop-stop stretches (SSS) within a gene sequence that contain an exon. In particular, all SSS regions within a gene sequence are first identified (step S.240). As part of this step, SSS regions in all three reading frames and in all three reverse reading frames may be located and identified. Thereafter, the score of each SSS region is calculated (step S.244). In this regard, the DiCTion function and features and aspects of FIG. 3 of the invention may be utilized to determine the score of an SSS region.

As further illustrated in FIG. 10, following step S.244, a determination is made as to whether the score of the SSS region is above a predetermined threshold (step S.248). This threshold may be set to a value of 1.0 or 1.5. If the score of the SSS region is greater than or equal to the predetermined threshold, then the SSS region is identified as containing an exon (step S.252). If, however, the score of the SSS region is not greater than or equal to the predetermined threshold, then the SSS region is identified as not containing an exon (step S.256). If it is determined that additional SSS regions are to be examined (step S.260), then logic flow loops back to analyze the scores of the additional SSS regions (step S.244-S.256). Otherwise, as illustrated in FIG. 10, the process terminates.

The embodiment of FIG. 10 can be utilized to determine the approximate regions of long exons within a gene. While this embodiment may overlook small exons and fail to accurately predict the presence of an exon if an SSS region is significantly longer than the exon that it contains, this aspect of the invention has in fact been tested and determined to correctly identify the approximate position of exons in thirty-two different genes.

FIG. 11 is an exemplary flowchart of the various operations and processes for performing a fine level analysis of genes, in accordance with an embodiment of the invention. While the exact positions of exons within a gene can be determined using the border detection techniques and other features and aspect of the present invention, such an approach may be computationally intensive and not suited for all applications. In such cases, the fine level analysis embodiment of FIG. 11 can be utilized to provide an alternative process for predicting the positions of exons. As further described below, the embodiment of FIG. 11 utilizes what is referred to as a jumping window to analyze a given sequence and detect the presence of an exon. A jumping window may be set to a predetermined, fixed length (e.g., 100 bases) and may overlap with other jumping windows by moving or jumping the window a fixed number of bases (e.g., 10 bases) from the beginning to the end of the identified gene (i.e., bases 1–100, 10–110, 20–120, etc.).

As illustrated in FIG. 11, the first jumping window in the sequence of the gene is initially identified (step S.280). Assuming a fixed jumping window size of 100 bases, the first jumping window would be set at bases 1–100. Thereafter, the score of the jumping window is calculated (step S.282). The score of the jumping window can be calculated using the DiCTion function and features and aspect of FIG. 3, described above. If the score of the jumping window is determined to be greater than or equal to a predetermined threshold (step S.284), then the jumping window is flagged for further analysis (step S.286). If, however, the score of the jumping window is not greater than or equal to the predetermined threshold, then a determination is made as to whether the end of the gene has been reached (step S.288). In other words, it is determined whether additional jumping windows are to be identified and analyzed for the given gene. If additional jumping windows exist, then the next jumping window is identified (step S.290) and logic flow loops back in order to calculate the score of the jumping window and analyze whether the score is above the predetermined threshold (step S.282-S.284).

The process of calculating a score for each jumping window and flagging windows that have a significant score continues until the end of the gene is reached (step S.288-Yes). After examining all of the jumping windows, each flagged window is examined to determine the exact position of exons within the gene. As illustrated in FIG. 11, the borders or ends of each flagged jumping window is expanded until a maximum score is reached (step S.292). In this regard, the border detection techniques and features of FIGS.5A and 5B can be utilized to individually expand the borders or ends of each flagged jumping window. Thereafter, the longest expanded window is identified (step S.294) and the position of the exon and the borders of the exon are determined based on the longest expanded window (step S.296). The position of the exon or coding region is more likely to be present in the longest of the expanded flagged windows. However, exons may be also present in the other expanded flagged windows and, therefore, these portions of the gene may also be analyzed for the presence of an exon.

Although the disclosed jumping window approach resembles the sliding window approach of past approaches, the jumping window technique of the present invention is unique in that further analysis is done after the windows are identified. Specifically, even when a jumping window is utilized, the goal is still to use as much of the sequence information as possible be expanding the window until the exact borders of the coding region are identified.

FIGS. 12 and 13 illustrate, in accordance with another embodiment of the present invention, alternative fine level analysis processes for determining the positions of exons within a sequence of a gene. By identifying a point of interest (P1 or P2) and analyzing the scores of a fixed-length window (e.g., a window of a 100 bases) on either side of the point of interest, the ends of an exon can be determined by comparing the scores on both sides. In the embodiments of FIGS. 12 and 13, the ends of exons are identified based on the principal that the difference between the scores will be maximized when the point is at the border between coding and non-coding sequences. The point of interest can then be moved for locating the 5' and 3' borders. In order to improve the precision of this analysis, the scores of the windows may be determined at every position. In addition, a new "uborder scoring function" may be applied based on a ratio or sum or difference of DiCTion scores, as further discussed below.

As illustrated in FIG. 12, a significant window is first identified in the sequence of the gene (step S.330). This window may be of a fixed length (e.g., 100 bases) and may be determined to be "significant" based on the determination that the score of the window is greater than or equal to a predetermined threshold (e.g., 1 or 1.5). After identifying the significant window in the gene, a point of interest (P1) is assigned to the upstream end of the significant window (step S.332). This point of interest P1 is used as a central point between additionally defined windows of fixed length (e.g., 100 bases), in order to identify the border between coding and non-coding regions. As such, fixed windows are created on the upstream and downstream sides of P1 and the scores of the fixed windows on both sides of P1 are calculated (step S.334). Once again, each score may be calculated using the DiCTion function of the present invention. After calculating the scores of each window, the calculated scores are recorded (step S.336).

As further illustrated on FIG. 12, a determination is then made whether the upstream border or 5' border is detected (step S.338). In terms of detecting a 5' border, the presence of such a border is detected based on scores that indicate the upstream window to be non-coding and the downstream window to be coding. A fixed window may be determined to indicate the presence of a coding region or non-coding region based on whether or not the score of the window is greater than or equal to a predetermined threshold (e.g., 1 or 1.5). If the 5' border between a non-coding and a coding region is not detected, then the point of interest P1 is moved upstream of the sequence of the gene (step S.340). In this regard, the point of interest P1 may be moved codon by codon upstream of the sequence until the 5' border is detected. That is, by repeating steps S.334 through S.338 in FIG. 12, the scores of fixed windows on each side P1 may be analyzed until the characteristics of the 5' border are detected. Once the 5' border is detected (step S.338-Yes), the 5' border is identified (step S.342) in the sequence of the gene and the process terminates.

As illustrated in FIG. 13, a similar process to that described above in relation to FIG. 12 can be utilized to detect the downstream end or 3' border of the exon. In particular, such a process is initiated by first identifying a significant window in the gene (step S.350). The significant window may be the same window that was identified in step S.330 in FIG. 12, or may be another window with a significant score. Following step S.350 in FIG.13, a second point of interest P2 is assigned to the downstream end of the significant window (step S.352). Fixed windows are then defined on either side of the point of interest P2 and scores are calculated for each of the windows (step S.354). Once again, the windows may be of a predetermined, fixed length (e.g., 100 bases) and may be moved as the point of interest P2 is moved along the gene sequence. After the scores of each window is calculated, they are recorded for future analysis (step S.356).

In order to determine whether the downstream or 3' border has been detected (step S.358), a the scores for the upstream window and downstream window are compared to a predetermined threshold and the presence or absence of a coding region or a non-coding region is determined. For the purposes of detecting the 3' border, a coding region should be present upstream of the point of interest P2, and a non-coding region should be present downstream of P2. If the characteristics of a 3' border is detected then the position of P2 in the gene sequence is identified as the 3' border (step S.362). If, however, the 3' border is not detected (step S.358-No), then P2 is moved downstream of the sequence by one codon (step S.360) and steps S.354-S.358 in FIG.13 are repeated until the 3' border is detected. After identifying the 3' border (step S.362), the process of FIG. 13 terminates.

As a modification to the embodiments of FIGS. 12 and 13, a border score may be defined such that the score (as computed by a scoring function) will be maximized at the border between coding and non-coding regions. Under this approach, such a score may be calculated at every possible position and the maximum identified. Examples of a border scoring function include a ratio of scores technique, in which the ratio of DiCTion scores for approximately 100 bases before the putative border or point of interest, and for approximately 100 bases after the putative border or point of interest is computed. Another example of a border scoring function is the difference between the DiCTion scores of approximately 100 bases before the putative border and that of a 100 bases after. Still another example of a scoring function is a sum of scores technique, in which all of the scores before the putative border or point of interest are summed and influenced in some form by the index in order to determine a maximum.

The features of the present invention may also be utilized for identifying cDNA sequences in a known gene sequence. For example, the DiCTion function and border detection techniques of the invention can be utilized to provide major clues for identifying cDNAs by providing at least an approximate starting position for a given gene. A primer designed for this sequence could then be used to isolate the appropriate cDNA from a library or database.

Complete genomes for many organisms are becoming widely available and, within the foreseeable future, the complete human genome will also likely be available. With all this sequence information, it will become increasingly important to identify the loci of genes within genomes. To this end, the present invention can also provide a useful tool for analyzing and determining information about genomes. For example, given the sequence of a whole chromosome, the features of the present invention can be applied to identify regions of interest in the sequence, such as the loci of genes which are clusters of coding regions. By way of a non-limiting example, assuming that the genome information is known, the loci of genes can be determined with the features of the invention by performing the following main steps: (i) identifying all stop-stop stretches (SSS) whose DiCTion score is greater than or equal to a predetermined threshold; (ii) clustering all putative coding regions that are identified; and (iii) identifying the loci of genes based on the principal that the average distance between genes will be larger than the average distance between exons within the same gene. The above described process may be well suited for microbial genomes (e.g., Methanococcus jannaschii, Mycobacterium tuberculosis) which are not expected to have any introns and hence, all their "exons" will be full proteins.

As will be apparent from above-described applications of the invention, given the sequence of a genome, the features of the invention can be used iteratively to identify genes, the coarse regions of exons within the genes and then fine level analysis of the position of the exon borders to ascertain the likely sequence of a cDNA corresponding to the gene. With this information, a skilled molecular biologist or researcher will be able to isolate the cDNAs and then obtain the protein that it expresses from the same organism as well as from closely related species. Therefore, the features of the invention, in conjunction with for example molecular biology experiments, can be useful in the entire array of applications related to genome analysis.

As indicated above, the disclosed DiCTion function of the present invention is not dependent on the species from which the sequence is derived. The DiCTion function and features of the invention have been successfully applied to sequences from human, prokaryotic, C. elegans and many other species. This ability is due to the fact that the DiCTion function measures a property that appears to be required for any sequence to be coding. In the rare cases where there is a change in the genetic code, appropriate changes should be made to the definition of an ORF. This may occur, for example, when looking at mitochondrial sequences.

Referring now to Table 5, an example will be provided to illustrate the effectiveness and accuracy of the features of the present invention as applied to coding sequences for non-human species. In this example, the DiCTion function and principles of the invention are applied to fifty sequences, all from non-human sources. The sequences and their corresponding score are indicated in Table 5 below.

TABLE 5

Coding Sequences from Non-human Species and their DiCTion Score

| Accession | Species | Score |
|---|---|---|
| ab003472.gb_ov | Trimeresurus flavoviridis | 1.530516432 |
| ab010103.gb_ov | Danio rerio | 0.85560675883 |
| ab013499.gb_pl1 | Schizosaccharomyces pombe | 4.09765625 |
| ab013912.gb_ro | Mus musculus | 11.6338971106 |
| ab015611.gb_pl1 | Mortierella alpina | 12.4746963563 |
| ab016599.gb_pl1 | Saccharomyces cerevisiae | 27.6933621934 |
| ab017628.gb_in1 | Schizosaccharomyces pombe | 3.2494949495 |
| ab018405.gb_new | Coriolus versicolor | 11.1383981154 |
| af007874.gb_in2 | Caenorhabditis briggsae | 2.22580645161 |
| af014812.gb_pl2 | Emericella nidulans | 4.78244274809 |
| af018093.gb_pl2 | Pisum sativum | 3.18177387914 |
| af030169.gb_ro | Mus musculus | 6.60709759189 |
| af044574.gb_ro | Rattus norvegicus | 4.8704954955 |
| af045473.gb_pl2 | Zea mays | 10.1357350801 |
| af047046.gb_new | Mus musculus | 5.13471177945 |
| af047601.gb_new | Mus musculus | 17.0393817204 |
| af059310.gb_pl2 | Saccharomyces cerevisiae | 3.14455782313 |
| af067792.gb_pl2 | Arabidopsis thaliana | 2.93852459016 |
| af071564.gb_ov | Crotalus adamanteus | 6.520755886 |
| af074718.gb_ro | Mus musculus | 2.41637220259 |
| af082565.gb_new | Arabidopsis thaliana | 28.6883848134 |
| af085717.gb_new | Gossypium hirsutum | 2.40340909091 |
| af086820.gb_in2 | Drosophila melanogaster | 7.3466819222 |
| af087672.gb_new | Mus musculus | 9.09253417455 |
| af098068.gb_ro | Mus musculus | 13.242 |
| af098916.gb_new | Dictyostelium discoideum | 26.0535929952 |
| af101078.gb_in2 | Caenorhabditis elegans | 21.718925421 |
| af105076.gb_pl2 | Schizosaccharomyces pombe | 3.7886977887 |
| af105333.gb_in2 | Drosophila melanogaster | 11.8807234432 |
| af108944.gb_pl2 | Aspergillus niger | 28.4401073936 |
| af118106.gb_new | Danio rerio | 3.89508196721 |
| af119388.gb_new | Caenorhabditis elegans | 4.52056737589 |
| af130865.gb_new | Metarhizium anisopliae | 9.97741147741 |
| af132445.gb_new | Danio rerio | 3.86894977169 |
| af132447.gb_new | Danio rerio | 2.13112745098 |
| af139659.gb_new | Mus musculus | 1.81780167264 |
| af143493.gb_new | Danio rerio | 14.7444643926 |
| af146517.gb_new | Caenorhabditis elegans | 1.0395256917 |
| af148501.gb_new | Schizophyllum commune | 21.382973251 |
| af149421.gb_new | Candida albicans | 6.69645732689 |
| d01035.gb_pl1 | Asperigillus oryzae | 8.19313884387 |
| d11386.gb_pl1 | Saccharomyces cerevisiae | 2.95547945205 |
| d82039.gb_pl1 | Oryza sativa | 8.28293807642 |
| j02684.gb_ov | Bothrops atrox | 2.15436654367 |
| u10638.gb_ov | Brachydanio rerio | 3.68482490272 |
| u28804.gb_pl2 | Emericella nidulans | 6.58355205599 |
| u55321.gb_in2 | Drosophila melanogaster | 8.78053624628 |
| u68185.gb_in2 | Caenorhabditis elegans | 4.60084427767 |
| u86634.gb_ov | Agkistrodon contortrix laticinctus | 4.79095607235 |
| u92044.gb_in2 | Caenorhabditis elegans | 3.30151515152 |

In the example of Table 5, there are two false negatives (i.e., coding sequences with a DiCTion score below 1.5) that are identified in bold in the table. Although the total number of coding sequences used in this example is not sufficient to evaluate statistical significance, the results are consistent with the 95% accuracy seen in the larger experiment or study. Further, the results of this example combined with the tested performance of the invention on human sequences, indicates that the present invention will work well with any species (e.g., microbial genomes such as Methanococcus jannaschii and Mycobacterium tuberculosis). This is because DiCTion and the features of the present invention appear to tap into a fundamental property of all coding sequences. Further, there is no scientific reason that would lead to the conclusion that non-human sequences are fundamentally different from human sequences. In addition, in order to investigate the level of false positives generated by the invention for non-human species, a further study was performed on 37,883 sequences of 3' UTR and 33,008 sequences of 5' UTR from many non-human species. As a result of this analysis, a false positive rate of 1.01% was found among 3' UTR sequences. Further, a false positive rate of 0.4% was found among 5' UTR sequences. These levels of false positives are acceptable for most applications and further illustrates how well suited the features of the invention are for analyzing sequences of non-human species.

It will be apparent to those skilled in the art that various modifications and variations can be made to the invention without departing from the scope or spirit of the invention. For example, while certain aspects and features of the invention have been described with reference to analyzing cDNA sequences and open reading frames (ORFs), the principles of the invention may be applied to any DNA or RNA sequence. For example, the disclosed DiCTion functions and features of the present invention may be applied to any genomic DNA sequence to distinguish between coding and non-coding regions. That is, by analyzing the regions of a given sequence between pairs of termination codons, splice sites, or ORFs, the features of the present invention can be utilized to detect coding regions within any genomic DNA sequence. Further, once the coding regions within a sequence are identified, the border detection techniques and other features of the invention may be applied to gather additional information from any sequence.

Other modifications can be made to the disclosed embodiments of the invention. For example, while the features of the invention have been described with reference to the DiCTion function, other cosine-based functions or Fourier transform functions may be utilized to measure the periodicity in DNA sequences. By way of a non-limiting example, a Fourier transform function, such as that disclosed in TIWARI et al. (1997), may be adapted and implemented according to the principles of the invention in order to analyze and score regions within a DNA sequence. In such a case, the Fourier transform function should be calculated at only one frequency (i.e., a ⅓ frequency), with the Fourier transform at all other frequencies being ignored. Further, when analyzing the periodicity of the sequence, there is no need to analyze the signal to noise ratio or to use a sliding window. Instead, all open reading frames (ORFs) of a suitable length (e.g., ORFs greater than 150 nucleotides) can be analyzed and scored with the Fourier transform function, and coding regions can be determined by comparing the score of the ORF to a predetermined threshold. In all cases, the predetermined threshold should be set to a level (e.g., 0.5, 1.0, 1.5, 2.0, 2.5, etc.) that provides the best overall combination of sensitivity and specificity. Further, in order to eliminate frame dependency, an index may be determined for each ORF, in a similar manner to that described above with reference to FIG. 3. For genomic DNA sequences other than cDNA sequences, regions between termination codons or splice sites may be examined instead of ORFs.

In order to illustrate the manner in which other scoring functions may be substituted for the DiCTion function disclosed herein, assume for example that the Fourier transform function disclosed in TIWARI et al.(1997) is applied to the embodiments of the invention. In such a case, the Fourier transform function would be calculated at a frequency of ⅓ for all ORFs within the sequence. Using the sequence data of Bullet Train and Control DB, a threshold value of 0.5 (i.e., considering all sequence regions that have a score greater than or equal to 0.5 to be coding) produces 2 false negatives (Bullet Train sequences predicted to be non-coding) and 1171 true negatives (674+487 UTR sequences predicted to be non-coding). In other words, approximately 0.2% of the Bullet Train database, 10% of the 3' UTR database and 33.8% of the 5' UTR database. To improve these results, a different threshold value can be selected so that most of the UTRs score below the threshold and most of the Bullet Train sequences score above it, thus minimizing the false negatives and false positives. If, for example, the threshold is set to 2.5, then using the Fourier transform function of TIWARI et al. will reject 93.7% of 3' UTRs, 89% of 5' UTRs and 9.6% of Bullet Train. In such a case, the false negative rate is 9.6% and the false positive rate is between 7 to 11%. While these results are inferior to the results provided by the present invention (see, for example, Table 2), such results are better than that reported by TIWARI et al. for the Fourier transform analysis technique disclosed in that reference.

The above example illustrates that while the DiCTion function of the present invention is the best measure of periodicity for detecting coding potential, other measures of periodicity such as a Fourier transformation function can also be utilized. In all cases, however, the other components of the DiCTion function and present invention (i.e., ignoring signal to noise analysis and checking ORFs instead of sliding windows) should be maintained in order to improve the performance of the periodicity function.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for analyzing a nucleic acid sequence, said method comprising:

provciding nucleic acid sequence data;

identifying, based on the nucleic acid sequence data, each open reading frame (ORF) of the nucleic acid sequence;

calculating a score for each identified ORF of the nucleic acid sequence, wherein said calculating comprises examining the periodicity of each base in each identified ORF at a frequency of ⅓;

comparing the calculated score of each ORF to a predetermined threshold; and identifying at least one probable protein-coding region in the nucleic acid sequence based on the comparison of the score of each ORF to the predetermined threshold.

2. A method according to claim 1, wherein said examining comprises determining a score, D(F), for each ORF based on the following:

$$D(F) = \frac{1}{N} \sum_{\alpha} \left| \sum_{j=1}^{N} U_{\alpha}(j)\cos(2\pi F j) \right|^2$$

where F is a frequency of ⅓; N is the number of nucleotides in the ORF; $\alpha$ varies over four bases including Adenine (A), Cytosine (C), Guanine (G), and Thymine (T) or Uracil (U); j is a position in the ORF; and $U_\alpha(j)$ is a delta function.

3. A method according to claim 2, wherein said identifying at least one probable protein-coding region comprises identifying every ORF having a score greater than or equal to the predetermined threshold as corresponding to a coding region.

4. A method according to claim 3, wherein the predetermined threshold is 1.5.

5. A method according to claim 1, Wherein said examining comprises scoring the periodicity of each base in the ORF at a frequency of ⅓ based on a cosine-based function.

6. A method according to claim 5, wherein said scoring comprises determining an index of each ORF based on the index assigned to the first base of each ORF that provides a maximum score, and setting the score for each ORF to the maximum score at the index.

7. A method according to claim 1, wherein said identifying each ORF in the nucleic acid sequence comprises locating an initiation codon and a termination codon that is in-frame.

8. A method according to claim 1, wherein said method further comprises determining each border of an identified probable coding region in the nucleic acid sequence.

9. A method according to claim 8, wherein said determining each border comprises arbitrarily setting two border locations in the identified probable coding region of the nucleic acid sequence, calculating a score for the portion of the sequence between the two border locations, and moving one of the two border locations along the nucleic acid sequence until a maximum score is calculated.

10. A method according to claim 1, wherein said nucleic acid sequence is a cDNA sequence, a genomic DNA sequence, or an RNA sequence.

11. A computer program product comprising computer-readable media having computer-readable code which, when run on a computer, causes the computer to analyze a nucleic acid sequence based on a set of nucleic acid sequence data, the computer program product comprising the following computer-readable program code for effecting actions in the computer:

program code for identifying, based on the nucleic acid sequence data, each open reading frame (ORF) of the nucleic acid sequence;

program code for calculating a score for each identified ORF of the nucleic acid sequence, wherein said calculating comprises examining the periodicity of each base in each identified ORF at a frequency of ⅓;

program code for comparing the calculated score of each ORF to a predetermined threshold and for determining whether the score of the ORF is greater than or equal to the predetermined threshold; and program code for identifying a probable coding region in the nucleic acid sequence based on the score of each ORF that is determined to be greater than or equal to the predetermined threshold.

12. A computer program product according to claim 11, wherein said program code for identifying a probable coding region comprises program code for identifying each ORF having a score greater than or equal to a threshold of 1.5 as corresponding to a coding region.

13. A computer program product according to claim 11, wherein said program code for examining comprises program code for determining a score, D(F) for each ORF based on the following:

$$D(F) = \frac{1}{N} \sum_{\alpha} \left| \sum_{j=1}^{N} U_{\alpha}(j)\cos(2\pi F j) \right|^2$$

where F is set to a frequency of ⅓; N is the number of nucleotides in the ORF; α varies over four bases including Adenine (A), Cytosine (C), Guanine (G), and Thymine (T) or Uracil (U); j is a position in the ORF; and $U_\alpha$(j) is a delta function.

14. A computer program product according to claim 11, wherein said program code for examining comprises program code for scoring the periodicity of each base in the ORF at a frequency of ⅓ with a cosine-based function.

15. A computer program product according to claim 14, wherein said program code for scoring comprises program code for determining an index of each ORF based on the index assigned to the first base of each ORF that provides a maximum score, and program code for setting the score for each ORF to the maximum score at the index.

16. A computer program product according to claim 11, wherein said program code for identifying each ORF in the nucleic acid sequence comprises program code for locating an initiation codon and a termination codon that is in-frame.

17. A computer program product according to claim 11, wherein said computer program product further comprises program code for determining, based on the nucleic acid sequence data, each border of an identified probable coding region in the nucleic acid sequence.

18. A computer program product according to claim 17, wherein said program code for determining each border comprises program code for arbitrarily setting two border locations in the identified probable coding region of the nucleic acid sequence, program code for calculating a score for the portion of the sequence between the two border locations, and program code for moving one of the two border locations along the nucleic acid sequence until a maximum score is calculated.

19. A computer program product comprising computer-readable media having computer-readable code which, when run on a computer, causes the computer to analyze a nucleic acid sequence based on a set of sequence data, the computer program product comprising the following computer-readable program code for effecting actions in the computer:
  program code for identifying, based on the nucleic acid sequence data, predetermined regions of the nucleic acid sequence;
  program code for calculating a score for each identified region of the nucleic acid sequence, wherein said calculating comprises examining the periodicity of each base in each region at a frequency of ⅓;
  program code for comparing the calculated score of each region to a predetermined threshold; and
  program code for identifying a probable coding region in the nucleic acid sequence based on the comparison of the score of each region to the predetermined threshold, wherein said program code for identifying a coding region comprises program code for identifying each open reading frame (ORF) having a score greater than or equal to the predetermined threshold as corresponding to a probable coding region.

20. A computer program product according to claim 19, wherein said computer program product further comprises program code for determining, based on the sequence data, each border of an identified probable coding region in the nucleic acid sequence.

21. A computer program product according to claim 20, wherein said program code for determining each border comprises program code for arbitrarily setting two border locations in the identified probable coding region of the sequence, program code for calculating a score for the portion of the sequence between the two border locations, and program code for moving one of the two border locations along the sequence until a maximum score is calculated.

22. A computer program product comprising computer-readable media having computer-readable code which, when run on a computer, causes the computer to analyze a nucleic acid sequence based on a set of sequence data, the computer program product comprising the following computer-readable program code for effecting actions in the computer:
  program code for identifying predetermined regions of the nucleic acid sequence based on the sequence data;
  program code for calculating a score for each identified region of the nucleic acid sequence, wherein said calculating comprises examining the periodicity of each base in each region at a frequency of ⅓;
  program code for comparing the calculated score of each region to a predetermined threshold; and
  program code for identifying a probable coding region in the nucleic acid sequence based on the comparison of the score of each region to the predetermined threshold, wherein said program code for identifying predetermined regions comprises program code for locating each region of the nucleic acid sequence that is between pairs of in-frame termination codons.

23. A computer program product according to claim 22, wherein said computer program product further comprises program code for determining, based on the sequence data, each border of an identified probable coding region in the nucleic acid sequence.

24. A computer program product according to claim 23, wherein said program code for determining each border comprises program code for arbitrarily setting two border locations in the identified probable coding region of the sequence, program code for calculating a score for the portion of the sequence between the two border locations, and program code for moving one of the two border locations along the sequence until a maximum score is calculated.

25. A computer program comprising computer-readable media having computer-readable code which, when run on a computer, causes the computer to analyze a nucleic acid sequence based on a set of sequence data, the computer program product comprising the following computer-readable program code for effecting actions in the computer:
  program code for identifying predetermined regions of the nucleic acid sequence based on the sequence data;
  program code for calculating a score for each identified region of the nucleic acid sequence, wherein said calculating comprises examining the periodicity of each base in each region at a frequency of ⅓;
  program code for comparing the calculated score of each region to a predetermined threshold; and
  program code for identifying a probable coding region in the nucleic acid sequence based on the comparison of the score of each region to the predetermined threshold, wherein said program code for identifying predetermined regions comprises program code for locating each region of the nucleic acid sequence that is between an initiation codon and an in-frame termination codon.

26. A computer program product according to claim 25, wherein said computer program product further comprises program code for determining, based on the sequence data, each border of an identified probable coding region in the nucleic acid sequence.

27. A computer program product according to claim 26, wherein said program code for determining each border comprises program code for arbitrarily setting two border locations in the identified probable coding region of the sequence, program code for calculating a score for the portion of the sequence between the two border locations, and program code for moving one of the two border locations along the sequence until a maximum score is calculated.

28. A computer program product comprising computer-readable media having computer-readable code which, when run on a computer, causes the computer to analyze a nucleic acid sequence based on a set of sequence data, the computer program product comprising the following computer-readable program code for effecting actions in the computer:

program code for identifying predetermined regions of the nucleic acid sequence based on the sequence data;

program code for calculating a score for each identified region of the nucleic acid sequence, wherein said calculating comprises examining the periodicity of each base in each region at a frequency of ⅓;

program code for comparing the calculated score of each region to a predetermined threshold; and program code for identifying a probable coding region in the nucleic acid sequence based on the comparison of the score of each region to the predetermined threshold, wherein said program code for identifying predetermined regions comprises program code for locating each region of the nucleic acid sequence that is between splice sites.

29. A computer program product according to claim 28, wherein said computer program product further comprises program code for determining, based on the sequence data, each border of an identified probable coding region in the nucleic acid sequence.

30. A computer program product according to claim 29, wherein said program code for determining each border comprises program code for arbitrarily setting two border locations in the identified probable coding region of the sequence, program code for calculating a score for the portion of the sequence between the two border locations, and program code for moving one of the two border locations along the sequence until a maximum score is calculated.

31. A method for locating at least one exon within a nucleic acid sequence, said method comprising:

identifying each region in the nucleic acid sequence that does not contain an internal stop codon;

calculating a score of each region in the nucleic acid sequence; and determining the location of at least one exon in the nucleic acid sequence based on the score of each region of the sequence, wherein said identifying comprises identifying each stop-stop stretch (SSS) region in the nucleic acid sequence and said calculating comprises scoring the periodicity of each base in each SSS region at a frequency of ⅓ in accordance with a periodicity function.

32. A method according to claim 31, wherein said determining comprises comparing the score of each SSS region in the sequence to a predetermined threshold and identifying an SSS region as containing an exon if the score of the SSS region is greater than or equal to the predetermined threshold.

33. A method for locating at least one exon within a nucleic acid sequence, said method comprising:

identifying at least one region in the nucleic acid sequence with a jumping window;

calculating a score of each region in the nucleic acid sequence;

comparing the score of each identified region in the sequence to a predetermined threshold and flagging the region if the score of the region is greater than or equal to the predetermined threshold;

expanding the borders of each flagged region until a maximum score for the flagged region is reached;

identifying the longest, expanded flagged region; and determining the location of an exon in the sequence based on the longest, expanded flagged region that is identified, wherein said calculating comprises scoring the periodicity of each base in each jumping window region at a frequency of ⅓ in accordance with a periodicity function.

34. A method according to claim 33, wherein said determining further comprises assigning a point-of-interest to one end of the identified region in the nucleic acid sequence, defining fixed window regions of the sequence on either side of the point-of-interest, calculating a score for each fixed window region, moving the point-of-interest by one codon along the sequence, recalculating the score for each fixed window region based on each movement of the point-of-interest, and determining at least one border of an exon in the sequence based on the calculated scores of each fixed window region.

35. A method for determining whether a protein coding region of a nucleic acid sequence is full length, said method comprising:

identifying a portion of the nucleic acid sequence that is upstream of the protein coding region of the sequence;

calculating a score for the upstream portion of the nucleic acid sequence; and determining whether the protein coding region is full length based on the calculated score of the upstream portion of the nucleic acid sequence, said determining comprising comparing the score of the upstream portion of the sequence to a predetermined threshold, wherein said calculating comprises examining the periodicity of each base in each region at a frequency of ⅓.

36. A method according to claim 35, said determining further comprising determining that the protein coding region is full length if the score of the upstream portion of the sequence is less than the predetermined threshold.

37. A method according to claim 35, said determining further comprising determining that the protein coding region is not full length if the score of the upstream portion of the sequence is greater than or equal to the predetermined threshold.

38. A method according to claim 35, wherein said calculating comprises determining a score, D(F) for the upstream portion of the sequence based on the following:

$$D(F) = \frac{1}{N} \sum_{\alpha} \left| \sum_{j=1}^{N} U_\alpha(j)\cos(2\pi F j) \right|^2$$

where F is set to a frequency of ⅓; N is the number of nucleotides in the upstream portion of the sequence; α varies over four bases including Adenine (A), Cytosine (C), Guanine (G), and Thymine (T) or Uracil (U); j is a position in the upstream portion of the sequence; and $U_\alpha(j)$ is a delta function.

39. A method according to claim 35, wherein said protein coding region is an open reading frame of the sequence, said identifying comprising locating the portion of the sequence that is upstream of an initiation codon of the open reading frame.

40. A method for determining whether a predetermined region of a nucleic acid sequence is full length, said method comprising:
identifying a portion of the nucleic acid sequence that is upstream of the predetermined region of the sequence;
combining the upstream portion of the sequence to the predetermined region of the sequence and calculating a score for the combined region; and
determining whether the predetermined region is full length based on the calculated score of the combined region, wherein said calculating comprises examining the periodicity of each base in each region at a frequency of ⅓.

41. A method according to claim 40, wherein said method further comprises calculating a score of the predetermined region of the sequence, and said determining comprises comparing the score of the combined region with the calculated score of the predetermined region and determining that the predetermined region is full length if the score of the predetermined region is greater than the score of the combined region.

42. A method according to claim 41, wherein said determining further comprises determining that the predetermined region is not full length if the score of the predetermined region is less than the score of the combined region.

43. A method according to claim 40, wherein said calculating comprises determining a score, D(F) for the combined portion of the sequence based on the following:

$$D(F) = \frac{1}{N} \sum_{\alpha} \left| \sum_{j=1}^{N} U_\alpha(j)\cos(2\pi F j) \right|^2$$

where F is set to a frequency of ⅓; N is the number of nucleotides in the combined portion of the sequence; α varies over four bases including Adenine (A), Cytosine (C), Guanine (G), and Thymine (T) or Uracil (U); j is a position in the combined portion of the sequence; and $U_\alpha(j)$ is a delta function.

44. A method according to claim 40, wherein said predetermined region is an open reading frame of the nucleic acid sequence, said identifying comprising locating the portion of the sequence that is upstream of an initiation codon of the open reading frame.

* * * * *